United States Patent [19]
Ladd et al.

[11] Patent Number: 5,324,512
[45] Date of Patent: Jun. 28, 1994

[54] [GLN']-LUTEINIZING HORMONE RELEASING HORMONE CONJUGATE OF TETANUS VACCINE AND ITS USES

[75] Inventors: Anna E. Ladd; Rosemarie B. Thau, both of New York, N.Y.; Yun-Yen Tsong, North Caldwell, N.J.

[73] Assignee: The Population Council, New York, N.Y.

[21] Appl. No.: 634,034

[22] Filed: Dec. 26, 1990

[51] Int. Cl.$^5$ .................. A61K 39/385; A61K 37/43; A61K 39/39; C07K 17/02
[52] U.S. Cl. ........................................ 424/88; 424/92; 530/313; 530/399; 530/403; 530/404; 530/405; 530/806; 530/807; 530/812
[58] Field of Search ................. 424/88, 92; 530/313, 530/399, 403, 806, 807, 812, 404, 405

[56] References Cited

U.S. PATENT DOCUMENTS

| | | | |
|---|---|---|---|
| 3,963,691 | 6/1976 | Hoffman et al. | 530/403 |
| 4,608,251 | 8/1986 | Mia | 424/88 |
| 4,676,981 | 6/1987 | Silversides et al. | 530/387 |
| 4,770,874 | 9/1988 | Allison et al. | 424/88 |
| 4,975,420 | 12/1990 | Silversides et al. | 424/88 |
| 5,036,047 | 7/1991 | Mia | 424/88 |
| 5,077,195 | 12/1991 | Blalock et al. | 435/6 |

FOREIGN PATENT DOCUMENTS 9011298 10/1990 World Int. Prop. O. .

OTHER PUBLICATIONS

Arimura et al (1975) Acta Endocrinologica 78:222–231.
Folkers et al (1981) J. Appl. Biochem. 3:263–271.
Byars et al (1987) Vaccine 5: 223–228.
Kennedy et al (1976) Clinica Chim. Acta 70:1–31.
Fraser et al., "Effect of Active Immunization to Luteinizing Hormone Releasing Hormone on Seruma and Pituitary Gonadotrophins, Testes and Accessory Sex Organs in Male Rat", J. Endocr., 63: 399–406 (1974).
Fraser et al., "LHRH Antibodies: Their Use in the Study of Hypothalamic LHRH and Testicular LHRH-like Material, and Possible Contraceptive Applications", In: Progress Toward a Male Contraceptive, Jeffcoate and Sandler, eds., New York, John Wiley, (1982) pp. 41–78.
Silverberg et al., "Cancer Statistics, 1988", CA 38:1–19 (1988). Accompanied by Editorial: The American Cancer Society, 75 years, Holleb.
Huggins et al., "Studies of Prostatic Cancer. Effect of Castration, of Estrogen, and of Androgen Injection on Serum Phosphatases in Metastatic Carcinoma of the Prostate", Cancer Res., 1:293–297 (1941).
Seftel et al., "Hormonal Therapy for Advanced Prostatic Carcinoma", J. Surg. Onc. Suppl., 1:14–20 (1989).
Beland et al., "Total Androgen Blockage for Metastatic Cancer of the Prostate", Am. J. Clin. Oncol., 11 (Suppl. 2):S187–S190 (1988).
Ravdin et al., "Active Immunization to Luteinizing Hormong Releasing Hormone to Inhibit the Induction of Mammary Tumors in the Rat", Life Sci., 43:117–123 (1988).
Chappel et al., "Active Immunication of Male Rhesus Monkeys Against Luteinizing Hormone Releasing Hormone", Biol. Reprod., 22:333–342 (1980).
Fraser et al., "Preparation of Antisera to Lutenizing Hormone Releasing Factor", J. Endrocrinol., 61:756–769 (1974).
Awoniyi et al., "Changes in Testicular Morphology in Boars Actively Immunized Against Gonadotropin Hormone-Releasing Hormone", J. Androl., 9:160–171 (1988).

(List continued on next page.)

Primary Examiner—Kay K. Kim
Attorney, Agent, or Firm—Brumbaugh, Graves, Donohue & Raymond

[57] ABSTRACT

The present prevention provides an effective, fast acting method of vaccination useful in suppressing gonadotropic hormone release. The vaccine utilizes LHRH conjugated at its amino terminus to a protein carrier and can be mixed with either adjuvants or detergents in order to provide an effect vaccine.

15 Claims, 11 Drawing Sheets

OTHER PUBLICATIONS

Steblay, "Glomerulonephritis Induced in Sheep By Injections of Heterologous Glomerular Basement Membrane and Freund's Complete Adjuvant", Exp. Med., 116:253–272 (1962).

Thau et al., "Effects of Immunication with the β-subunit of Ovine Luteinizing Hormone on Corpus Luteum Function in the Rhesus Monkey", Fertil. Steril., 31:200–204 (1979).

Dalsgaard, "Adjuvants", Vet. Immunol. Immunopathol., 17:145–152 (1987).

Talwar, "Immunobiology of Gonadotropin-Releasing Hormone", Steroid Biochem., 23:795–800 (1985).

Ellouz et al., "Minimal Structural Requirements for Adjuvant Activity of Bacterial Peptidoglycan Derivative", Biochem. and Biophys. Res. Comm., 59:1317–1325 (1974).

Jeffcoate et al., "Anti-LHRH Sera in the Investigation of Reproduction", In Edwards and Johnson, eds. Physiological Effects of Immunity Against Hormones, Cambridge: Cambridge University Press, pp. 121–136 (1976).

Nett et al., "A Radioimmunoassay for Gonadropin Releasing Hormone (Gn-RH) In Serum", J. Clin. Endocrinol. Metab., 36:880–885 (1973).

Copeland et al., "Luteinizing Hormone-Releasing Hormone: Sequential Versus Conformational Specificity of Antiluteinizing Hormone-Releasing Hormone Sera", Endocrinology, 104:1504–1512 (1979).

Arimura et al., "The Antigenic Determinant of the LH-Releasing Hormone for Three Different Antisera", Acta Endocrinol. Metab., 36:880–885 (1975).

Bercu et al., "Permanant Impairment of Testicular Development After Transient Immunological Blockage of Endogenous Luteinizing Hormone Releasing Hormone in the Neonatal Rat", Endocrinology, 101:1871–1879 (1977).

Sharpe et al., "The Influence of Sexual Maturation and Immunization Against LHRH on Testicular Sensitivity to Gonadotrophin Stimulation in vitro", Int. J. Androl., 1:501–508 (1978).

Ladd et al., "Active Immunization Against Gonadotrophin-Releasing Hormone Combined With Androgen Supplementation is a Promising Antifertility Vaccine for Males", Am. J. Rep. Immunol. and Microbiol., 17:121–127 (1988).

Takahashi et al., "Induction of CD8+ Cytotoxic T Cells by Immunization with Purified HIV-1 Envelope Protein in ISCOMS", Nature, 344:873–875 (1990).

Edelman, "Vaccine Adjuvants", Rev. Inf. Dis., 2:370–383 (1980).

Murray et al., "Mineral Oil Adjuvants; Biological and Chemical Studies", Annals of Allergy, 30:146–151 (1972).

Ladd et al., "Effects of Long-Term Immunization Against LHRH and Androgen Treatment on Gonadal Function", J. Reprod. Immunol., 15:85–101 (1989).

Clermont et al., "Quantitative Study of Spermatogenesis in the Hypophysectomized Rat", Endrocrinology, 57:369–382 (1955).

Shastri et al., "Important Role of the Carrier in the Induction of Antibody Response Without Freund's Complete Adjuvant Against a Self Peptide Luteinizing Hormone-Releasing Hormone (LHRH)", Am. J. Reprod. Immunol., 1:262–265 (1981).

Pique et al., "Specificity of anti-LHRH Antisera Induced by Different Immunogens", Immunochemistry, 15:55–60 (1978).

Carelli et al., "Immunological Castration by a Totally Synthetic Vaccine: Modification of Biological Properties of LHRH After Conjugation to Adjuvant-Active Muramyl Peptide", Int. J. Immunopharmacol., 7:215–224 (1985).

Hodges et al., "Long Term Suppression of Fertility by Immunication Against LHRH and its Reversibility in Female and Male Marmoset Monkeys", In: Recent Advances in Reproduction and Regulation of Fertility, Talwar, ed., Amsterdam: Elsevier, pp. 87–96 (1979).

[GLN⁸]-LUTEINIZING HORMONE RELEASING HORMONE CONJUGATE OF TETANUS VACCINE AND ITS USES

BACKGROUND OF THE INVENTION

The possibility of developing an antifertility vaccine for male mammals based on active immunization against Luteinizing Hormone Releasing Hormone (LHRH) is currently under investigation in several laboratories. These studies are based on the findings that antibodies against LHRH prevent gonadotropin release. Prevention of gonadotropin release causes regression of Leydig cells and suppression of testosterone production and spermatogenesis with subsequent infertility. See e.g. Fraser et al., "Effect of Active Immunization to Luteinizing Hormone Releasing Hormone on Serum and Pituitary Gonadotropins, Tests and Accessory Sex Organs in Male Rat", J. Endocrinol., 63:399-405 (1974); Fraser et al., "LHRH Antibodies: Their Use in the Study of Hypothalamic LHRH and Testicular LHRH-like Material, and Possible Contraceptive Applications", In: Sandlet, ed Progress Toward a Male Contraceptive. New York, John Wiley, (1982) pp. 41-78.

Production of anti-LHRH antibodies would also be useful to treat certain forms of cancer such as prostate cancer where such therapy could replace orchiectomy or LHRH analogue treatment.

Recurrent or metastatic cancer of the prostate is a major cause of cancer mortality in the United States with more than 25,000 deaths occurring annually because of this malignancy. Silverberg and Lubera, "Cancer Statistics", CA 38:1-19 (1988). It is the most common malignancy in men older than 70. Carcinoma within the prostate is a common finding at autopsy, being found in 20-40% of men between 70-79 years of age. Unfortunately, approximately one third of all prostate cancers are diagnosed only after the patient has clinically apparent disseminated disease with bone or visceral metastases outside the pelvis.

For patients with disseminated disease at the time of diagnosis the classical treatment is surgical orchiectomy. Huggins and Hodges, "Studies of Prostatic Cancer. Effect of Castration, Estrogen, and Androgen Injection of Serum Phosphatases in Metastatic Carcinoma of the Prostate", Cancer Res., 1:293-297 (1941). This procedure decreases serum testosterone levels by 95% and causes objective tumor regression in approximately 40% of cases and disease stabilization in an additional 40% of cases. Alternative strategies to surgical orchiectomy include treatment with diethylstilbestrol (DES) or with LHRH analogues. These strategies also seem to work by decreasing serum testosterone levels, and have similar response rates to those seen with orchiectomy. Results of first line single agent hormonal manipulations are favorable but average response durations are less than one year and actuarial survival less than 2 years. Seftel et al., "Hormonal Therapy for Advanced Prostatic Carcinoma", J. Surg. Onc. Suppl., 1: 14-20 (1989).

Recent results have suggested that the addition of an anti-androgen to initial orchiectomy or an LHRH antagonist may improve response rates. Using combined androgen blockade in patients with stage D2 prostate cancer, Labtie initially reported a 90% survival rate at 2 years. When this therapy was tested in a Canadian double-blinded randomized trial, the results still statistically significantly favored combined therapy although the improvement in survival was less striking (52% survival at 18 months with simple orchiectomy versus 66% survival with combined therapy). Beland et al., "Total Androgen Blockade for Metastatic Cancer of the Prostate", Am. J. Clin. Onc., 11 (Suppl. 2):S18714 S190 (1988) This modest but statistically significant improvement in survival provided by combined therapy was also seen in an American randomized study. Thus the optimal therapy for cancer of the prostate at this time seems to be a combination of orchiectomy and therapy that blocks peripheral androgen action.

Current therapies for the suppression of androgen production are not universally acceptable to all patients. Orchiectomy is psychologically unacceptable to many patients. The user of LHRH analogues is dependent on repetitive application of the analogue and involves long term inconvenience and expense. Use of estrogens such as DES is generally considered inferior to the other two treatment modalities due to cardiovascular complications and side effects such as gynecomastia.

Immunization against LHRH has been proposed as an alternative anti-neoplastic strategy for sex steroid dependent tumors. Raydin and Jordan, "Active Immunization to Luteinizing Hormone to Inhibit the Induction of Mammary Tumors in the Rat", Life Sci., 43:117-123 (1988). This strategy has been shown to be effective in animal models, and depends on the immunoneutralization of LHRH after active immunization of the host. This blockade of LHRH causes decreased production of gonadotropins and then secondarily decreased sex steroid production by the ovaries or testes. It would be of great significance in the treatment of this disease to have a LHRH vaccine capable of rapidly stimulating production of high titers of anti-LHRH antibodies.

The availability of synthetic LHRH has provided anti-LHRH antisera, needed for development of radioimmunoassays and immunocytochemistry. Unfortunately, the use of synthetic LHRH in humans to induce production of anti-LHRH antibodies is precluded by the necessity of using adjuvants not suitable for use in humans in order to achieve an effective titer within an acceptable time period. In the majority of the reported experiments, Freund's complete adjuvant (FCA) was used as an immune enhancer to obtain anti-LHRH antisera. Chappel et al., "Active Immunization of Male Rhesus Monkeys Against Luteinizing Hormone Releasing Hormone", Biol. Reprod., 22:333-342 (1974); Fraser et al., "Preparation of Antisera to Luteinizing Hormone Releasing Factor", J. Endocrinol , 61:756-769 (1974); and Awoniyi et al., "Changes in Testicular Morphology in Boars Actively Immunized Against Gonadotropin Hormone-Releasing Hormone", J. Androl., 9:160-171 (1988).

In developing vaccines for man, only materials permitted for use in humans can be utilized. This criterion eliminates FCA, the most potent immune enhancer. Thus other methods of inducing highly effective anti-LHRH antibody in the shortest possible time are necessary to enable anti-LHRH production in man. Steblay, "Glomerulonephritis Induced in Sheep By Injections of Heterologous Glomerular Basement Membrane and Freund's Complete Adjuvant", Exp. Med., 116:253-172 (1962); Thau et al., "Effects of Immunization with the ß-Subunit of Ovine Luteinizing Hormone on Corpus Luteum Function in the Rhesus Monkey", Fertil. Steril., 31:200-204 (1979); and Dalsgaard, "Adjuvants", Vet. Immunol. Immunopathol., 17:145-152 (1987).

The studies described below were designed to examine the ability of LHRH conjugated to tetanus toxoid (TT) either at the N-terminal, C-terminal, or mid-section of the LHRH to induce biologically effective antibodies in the shortest possible time.

It has now been shown that conjugating a protein carrier to LHRH enhances immunogenicity in a site specific manner. Carriers such as TT and purified protein derivative (PPD, derived from tuberculin) which are suitable for use in man and have been shown to stimulate the immune response are useful as the protein carrier. Fraser et al., (1982); Shastri et al., (1981); Talwar, "Immunobiology of Gonadotropin-Releasing Hormone", J. Steroid Biochem., 23: 795–800 ( 1985 ); and Ellouz et al., "Minimal Structural Requirements for Adjuvant Activity of Bacterial Peptidoglycan Derivative", Biochem. and Biophys. Res. Comm.,59:13-17-1325 (1974).

SUMMARY OF THE INVENTION

Figure 1A:
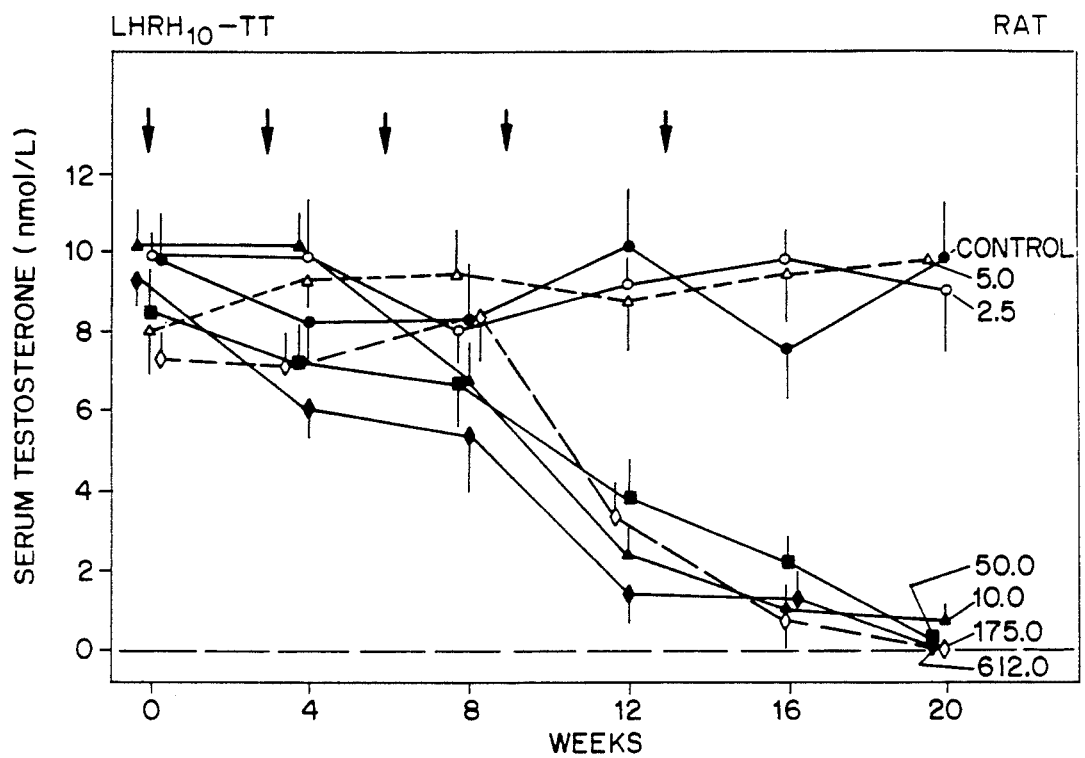
FIG. 1, discussed in Example 6, shows two graphs (A) and (B). Figure i(A) shows the serum testosterone levels
FIG. 1(B) shows the LHRH antibody titers in male rats immunized with increasing doses of $LHRH_{10}$-TT (nmol/L, mean±SE, n=12). The arrows indicate the time of immunogen injections.

The present invention is directed to both a method and a vaccine composition capable of inducing production of anti-LHRH antibodies. The anti-LHRH vaccine is based on the LHRH molecule conjugated at its amino terminal amino acid residue to a protein carrier such as TT ($LHRH_1$-TT) in combination with a physiologically acceptable diluent, vehicle and/or adjuvant. The method of inducing anti-LHRH antibodies includes vaccinating an animal with a quantity of the $LHRH_1$-TT vaccine sufficient to induce an effective titer of anti-LHRH antibodies in a suitable amount of time.

DETAILED DESCRIPTION OF THE INVENTION

The present invention shows that the conjugation site of a hapten to the LHRH molecule plays an important role in stimulating the immune system. Previous studies have shown that antibodies can be produced against unconjugated LHRH emulsified in FCA. For instance, using unconjugated LHRH in FCA, complete suppression of gonadal function was achieved in 100% of rats in 32 weeks with 8 injections. Several investigators reported that only a small percentage of animals immunized against unconjugated LHRH developed sufficient antibodies to suppress the biological actions of LHRH. Pique et al., ( 1978 ); Catelli et al., (1985); Hodges et al , ( 1979 ); and Jeffcoat et al., "Anti-LHRH Sera in the Investigation of Reproduction", In: Edwards and Johnson, eds. Physiological Effects of Immunity Against Hormones", Cambridge: Cambridge University Press, pp. 121–136 (1976).

A more uniform production of anti-LHRH antibodies could be achieved by conjugating the decapeptide LHRH to a carrier protein. Several proteins, such as bovine serum albumin (BSA), human serum albumin (HSA) thyroalobulin and tetanus toxoid (TT) have been tested as carrier molecules. Fraser et al., (1974); Nett et al., "A Radioimmunoassay for Gonadotropin Releasing Hormone (Gn-RH) In Serum", J. Clin. Endocrinol. Metab., 36:880–885 (1973); Copeland et al., "Luteinizing Hormone-Releasing Hormone: Sequential Versus Conformational Specificity of Antiluteinizing Hormone-Releasing Hormone Sera", Endocrinology, 104:1504–1512 (1979); Arimura et al., "The Antigenic Determinant of the LH-Releasing Hormone for Three Different Antisera", Acta Endocrinol Metab., 36:880–885 (1975); Copeland et al., (1979); Bercu et al., "Permanent Impairment of Testicular Development After Transient Immunological Blockade of Endogenous Lutenizing Hormone Releasing Hormone in the Neonatal Rat", Endocrinology, 101:1871–1879 (1977), and Sharpe et al., "The Influence of Sexual Maturation and Immunization Against LHRH on Testicular Sensitivity to Gonadotropin Stimulation in vitro", Int. J. Androl., 1:501–508 (1978). However, no systematic studies have been done to compare the effects of the conjugation sites of any hapten with the LHRH molecule on immunological and, consequently, biological responses. Thus a vaccine must be 100% percent effective and preferably work quickly, particularly in the case of carcinomas where a delay can be critical to the outcome. Although it has previously been shown that $LHRH_{10}$-TT suppresses gonadotropic hormones, the effect is not 100% complete until five months after therapy is initiated. This delay is far too long to allow the use of $LHRH_{10}$-TT in inducing infertility or in treating carcinomas. Ladd et al., "Active Immunization Against Gonadotropin-Releasing Hormone Combined With Androgen Supplementation is a Promising Antifertility Vaccine for Males", Am. J. Rep. Immunol. and Microbiol., 17:121–127 (1988).

It has now been found that the conjugation site of the LHRH molecule is critical to the immunological activity of LHRH. Mammals have now been found to respond to active immunization against LHRH conjugated to a TT at the N-terminus ($LHRH_1$-TT) by developing anti-LHRH antibodies capable of suppressing pituitary gonadotropin secretion significantly faster and more uniformly than animals immunized against $LHRH_6$-TT or $LHRH_{10}$-TT. $LHRH_1$-TT is the preferred embodiment of the present invention. Further, other protein carriers such as PPD (purified protein derivative obtained from tuberculin) and BSA have been found to form suitable conjugates. Thus, the invention is not limited to TT as a protein carrier; any immunogenic protein carrier suitable for use in humans is within the scope of the present invention. Unlike previously reported work, immunity to LHRH was accomplished by utilizing only materials permitted of use in humans.

$LHRH_1$-TT can be produced by the methods outlined below or by any suitable method known in the art of protein conjugation.

$LHRH_1$-TT is administered to subjects including but not limited to animals including man. In particular, subjects may include but are not limited to males with prostate or testicular carcinoma, benign prostatic hyperplasia and healthy males for the purpose of inducing infertility. Further, female subjects are included. In females, suppression of LHRH causes decreased estrogen and progesterone levels. Such treatment is suitable for a variety of disorders including but not limited to endometriosis, benign uterine tumors, recurrent functional ovarian cysts and severe premenstrual syndrome.

$LHRH_1$-TT is administered to a subject by any suitable method of injection including but not limited to parenteral, subcutaneous, intramuscular and intraperitoneal.

$LHRH_1$-TT is suspended in a sterile, physiologically acceptable vehicle prior to administration to a subject. Such vehicles include but are not limited to physiological saline, or an isotonic buffering compound. The vehicle may also include adjuvants including but not limited to murabutide, Freund's incomplete adjuvant, and Freund's complete adjuvant. In humans, adjuvants such as Freund's are not acceptable since they cause adverse reactions; for that reason only adjuvants suitable for use in humans are indicated when the subject is a human. For instance, the composition can be mixed with immunostimulating complexes as described by Takahashi et al., "Induction of CDS+Cytotoxic T Cells by Immunization With Purified HIV-1 Envelope Protein and ISCOMS", Nature 344:873–875 ( 1990 ).

As with all immunogenic compositions for eliciting antibodies, the immunogenically effective amounts of the composition of the invention must be determined empirically. Factors to be considered include the choice of adjuvant or carrier, the immunogenic molecule to which LHRH is coupled, the route of administration and the number of immunizing doses to be administered. Such factors are known in the vaccine art and it is well within the skill of immunologists to make such determinations without undue experimentation. Edelman, "Vaccine Adjuvants", Rev. Inf. Dis., 2:370–383 (1980). It has now been found that adjuvant is not necessary to induce an immune response utilizing the peptide of the present invention. As is described in detail below, when $LHRH_1$-TT is mixed with an isotonic solution containing detergents such as Tween 80 (also known as Polysorbate 80) and Pluronic L121, the vaccine is at least equally effective to vaccines containing commonly used adjuvants. This obviates the expense of these adjuvants and avoids any possible side effects inherent in their use. Although both TWEEN 80 (Polyoxyethylene (20) sorbitan monopoleate) and PLURONIC L121, a liquid block copolymer of propylene oxide and ethylene oxide, the liquid block copolymer having a molecular weight of approximately $3.5 \times 10^3$ and 15 weight percent ethylene oxide belong to a large group of related compositions, few of these related compositions are suitable for use in vaccines. The preferred composition is a mixture of Tween 80 and Pluronic L121. It is further preferred that they be combined in a range of proportion of 1 to 40, more preferably 1 to 25. Several other TWEENS or Pluronics are suitable for use in the present invention, but are thought to be less preferred. See e.g. Murray et al., "Mineral Oil Adjuvants; Biological and Chemical Studies", Anals of Allergy, 30:146–151 (1972).

The present invention is useful for inducing infertility in males and as an effective therapy for prostate cancer patients. In the case of prostate cancer treatment, the present invention can be used alone or in combination with other standard treatments such as orchiectomy or anti-androgen treatment. In addition, during treatment of men according to the present invention, androgen replacement therapy is recommended for maintenance of libido. A particularly suitable androgen supplementation is described in copending U.S. patent application No. 07/335,039, filed Apr., 7, 1989 to Bardin et al. which is incorporated herein by reference. U.S. patent application No. 07/335,039 describes compositions for androgen supplementation which are testosterone derivatives having a non-hydrogen substituent in the 6α or 7α position.

It has now been found that antibody production may not depend on the dose of an antigen ($LHRH_{10}$-TT), provided a minimal (threshold) dose has been surpassed. For instance, when $LHRH_1$-TT was used as an antigen, no differences in time course or magnitude of immune response was observed. Ineffective doses of $LHRH_1$-TT were not tested in this experiment, and therefore the threshold dose of this conjugate remains unknown. However, a complete suppression of testicular steroidogenesis, as evidenced by a marked decrease in serum T levels paralleled by the decrease in gonadal size (as estimated by palpation) was achieved 12 weeks faster than previously found. This decrease in time of suppression means that LHRH levels can now be suppressed within a therapeutically meaningful time frame, 4–8 weeks. Although in these experiments, mating to ensure infertility was not performed, in several of our previous experiments rats with testis size below 30% of normal and serum T levels below 0.03 nmol/L were infertile. Ladd et al., "Active Immunization Against Gonadotropin-Releasing Hormone Combined With Androgen Supplementation is a Promising Antifertility Vaccine for Males", Am. J. Reprod. Immunol., 17:121–127 (1988), and Ladd et al., "Effects of Long-Term Immunization Against LHRH and Androgen Treatment on Gonadal Function", J. Reprod. Immunol., 15:85–101 (1989).

The following experiments are provided to illustrate but not limit the present invention.

EXAMPLE 1

Synthesis of LHRH Conjugates

Synthetic LHRH with a free carboxyl terminal ($LHRH_{10}$-Gly-OH, code #139-183-20), [D-$Lys^6$]-LHRH, code #139-185-10, and [$Gln^1$]-LHRH, code #139-133-30 were generously provided by the Salk Institute (La Jolla, CA). Tetanus toxoid (TT) was obtained from the Wyeth Laboratory (Marietta, PA).

For conjugation, a solution consisting of 20 mg $LHRH_{10}$-Gly-OH, 20 mg purified TT, and 100 mg 1-ethyl-3-(3-dimethylaminopropyl)carbodiimide in a total volume of 20 mL water was incubated at room temperature for a 24 hour, followed by an 18 hour incubation at 4° C. The reaction mixture was dialyzed against distilled water for 2 days and lyophilized. The lyophilized $LHRH_{10}$-TT conjugate was used as an antigen. A similar procedure was used to conjugate TT at the N-terminal of [$Gln^1$]-LHRH and is described in Example 10.

$LHRH_6$-TT conjugate was prepared by reacting TT (25 mg in 0.9 mL of 0.1 M phosphate buffer) and 15 mg succinimidyl-4-(N-maleimidomethyl) cyclohexane-1-carboxylate in 1.1 mL dimethyl formamide at room temperature for 5 hours. The product was purified on a Sephadex G-25 column. The thiolated derivative of [D-$Lys^6$]-LHRH was prepared by reacting 12.3 mg [D-$Lys^6$]-LHRH in 1.2 mL of 0.1 M NaCl, 0.1 M phosphate buffer, pH 7.5, and 12.9 mg succinimidyl-3-(2-pyridyldithio) propionate in 1.2 mL dimethyl formamide. The reaction was carried out at room temperature for 3.5 hour. At the end of the reaction, 6.6 mg dithiothreitol was added, and the product was purified by Sephadex G-10 chromatography. The [D-$Lys^6$]-LHRH-TT ($LHRH_6$-TT) conjugate was prepared by reacting TT derivative and thiolated [D-$Lys^6$]-LHRH at room temperature for 24 h. The reaction product was dialyzed, lyophilized, and used as immunogen. N-acetyl normuramyl-L-alanyl-D-isoglutamine (MDP A-5, CIBA-GEIGY Limited, Basel, Switzerland) emulsified in a mixture of TWEEN 80 (0.2%) (Sigma Chemical) and PLURONIC L121 (2.5%) (BASF) in 0.9% NaCl (TP) was used as an adjuvant in the experiments provided below unless indicated otherwise.

EXAMPLE 2

Animals Used In Antisera Production

Sexually mature male rats (Sprague-Dawley, body weight 350–400 g) and rabbits (New Zealand White, body weight 3.3–3.6 kg, Dutchland, Denver, PA) were kept under standard conditions. The animals were immunized by subcutaneous injection at designated time intervals without anesthesia. Blood was collected from the middle caudal artery under ether-nembutal anesthesia (rats) and from the central ear artery (rabbits). The sera were separated and stored frozen until analyzed.

EXAMPLE 3

Radio immunoassays

Serum T was measured by radioimmunoassay (RIA) using a Coat-a-Count T Kit obtained from Diagnostic Products (Los Angeles, CA). Detection limits were from 0.01 to 0.03 pmol/L. Inter- and intra-assay coefficients of variation were 11.9 and 14.7%, respectively.

Serum luteinizing hormone (LH) and follicle stimulating hormone (FSH) levels were measured with RIA kits obtained from the National Hormone and Pituitary Program (Baltimore, MD). Rabbit FSH levels were expressed as ng/mL of AFP-538C. The limit of detection was 52 pg/mL. Rabbit LH levels were expressed as ng/mL of AFP-7818C. The limit of detection was 13 pg/mL. Rat LH levels were expressed as ng/mL of AFP-5666C. The limit of detection was 10 pg/mL. Rat FSH levels were expressed as ng/mL of AFT-4621B. All samples from each experiment were analyzed in duplicate in a single assay. RIA data were analyzed by a PDP-11/2 minicomputer.

EXAMPLE 4

LHRH Specific Antibody Titers

In the following experiments, LHRH antibody titers were determined by the following procedure. Antisera were diluted 1:100 in 1% bovine serum albumin (BSA) Sigma, St. Louis, MO). 100 μL of diluted antiserum were incubated overnight at room temperature in 1% BSA-precoated polystyrene tubes (100 μL) with 100 μL of [$^{125}I$]-LHRH (approximately 15,000 cpm). Antibody-bound [$^{125}I$]-LHRH was precipitated with 400 μL polyethylene glycol 8,000 (25% solution) and 200 μL of bovine γ-globulin (5 mg/mL). Antibody titers were expressed as nmoles of [$^{125}I$]-LHRH bound per liter of sera. Intra- and inter-assay coefficients of variation were 7.6 and 11.8%, respectively.

EXAMPLE 5

Tissue Preparation

At the end of each experiment, testes, epididymides, prostates, and seminal vesicles were removed and placed immediately into Bouin's solution for fixation. Following fixation, tissues were embedded in paraplast and cut into 5-μm slices. These were stained with periodic acid-Schiff/hematoxylin. The glass-mounted sections of the testes were evaluated under a light microscope as described by Clermont and Morgentaler, "Quantitative Study of Spermatogenesis in the Hypophysectomized Rat", Endocrinology, 57:369–386 (1955).

EXAMPLE 6

Effects of increasing doses of $LHRH_{10}$-TT Vaccine

Six groups of rats (12/group) were immunized against LHRH using 2.5, 5, 10 μg of $LHRH_{10}$-TT conjugate per rat. Rats were immunized by subcutaneous injection at weeks 0, 3, 6, and 10. Blood was collected every 4 weeks and analyzed for antibody titers (AT) and serum testosterone (T) levels. At the time of blood collection, testes were palpated to estimate their size as a semiquantitative criterion for success of the effect of the immunization.

Figure 1B:
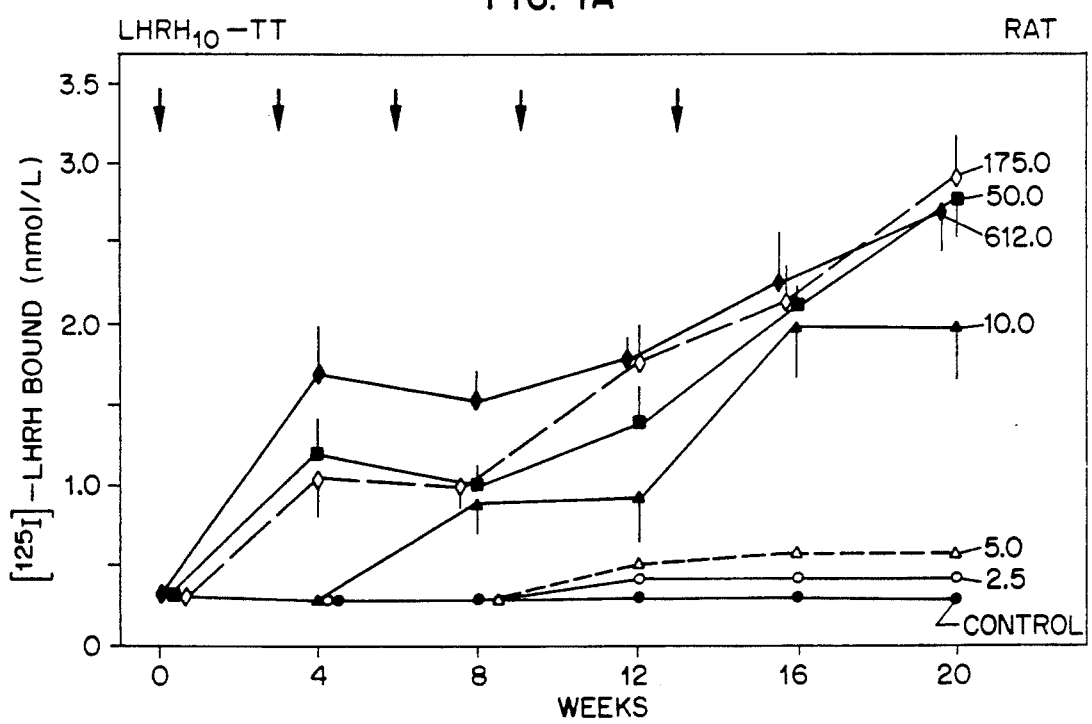

Rats immunized with either 2.5 or 5 μg of $LHRH_{10}$-TT developed barely measurable AT levels of 0.5 nmol/L in 5 and 7 of 12 rats in each group, respectively, by week 16. Ten μg of $LHRH_{10}$-TT per rat induced AT of $0.9 \pm 0.2$ nmol/L (mean±SE) at week 8. By week 16, AT levels reached 2 nmol/L in this group. Rats immunized with any of the three higher doses (50, 175, or 612 μg/rat) of $LHRH_{10}$-TT started developing antibodies faster than rats immunized with the dose of 10 μg of LHRH. Four weeks after the primary immunization, AT levels in the former groups ranged from 1 to 2 nmol/L. However, by week 8 there was no significant difference in antibody titers between the four groups of animals immunized with 50 or more μg/rat of $LHRH_{10}$-TT. This remained true until the end of the experiment, at week 20 (FIG. 1B).

Figure 2:
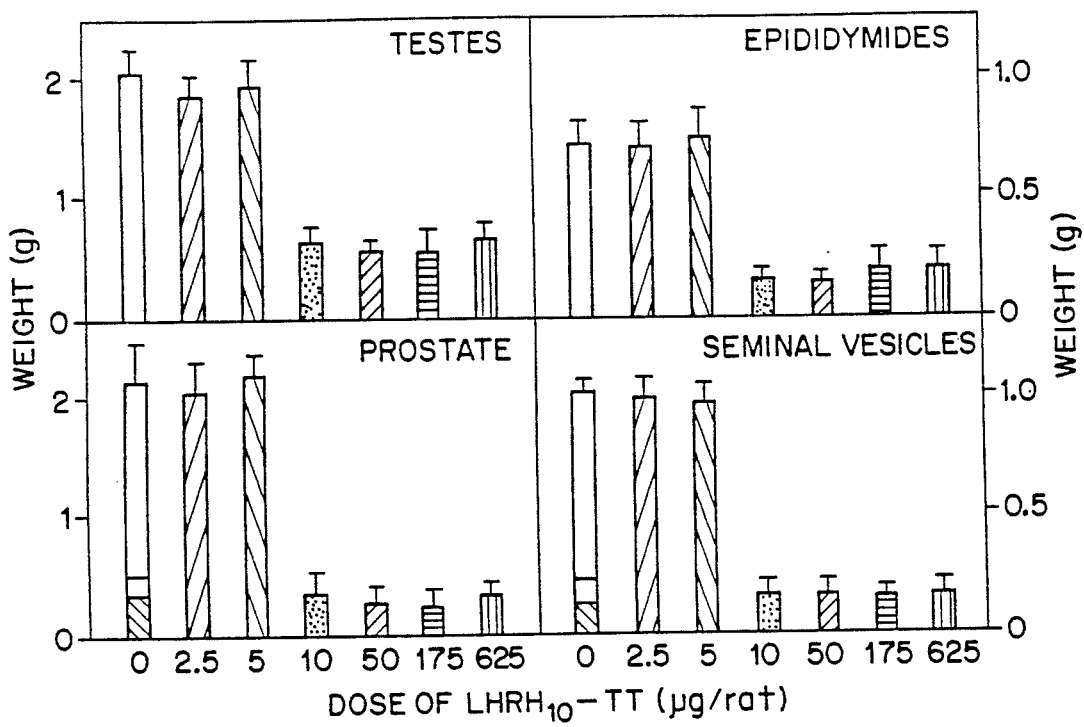
FIG. 2, discussed in Example 6, is a bar graph comparing the testicular and accessory sex organ weights of rats immunized with increasing doses of $LHRH_{10}$-TT 20 weeks after the primary immunization (mean±SE, n=11–12).

Rats immunized with either 2.5 or 5 μg of $LHRH_{10}$-TT had serum T levels similar to nonimmunized controls. Serum T levels in animals immunized with any of the higher doses of $LHRH_{10}$-TT (from 10 to 612 μg/rat) gradually declined and reached castration levels ($<0.03$ nmol/L) by week 20 (FIG. 1A). At this time the weights of testes and accessory sex organs in all groups of rats immunized with 10 μg/rat of $LHRH_{10}$-TT or more were significantly reduced as compared with nonimmunized controls or rats immunized with 2.5 or 5 μg of LHRH. The weights of the prostates and seminal vesicles were comparable with those of castrated rats. The reduction in weight of the testes and accessory sex organs was not dependent on the dose of $LHRH_{10}$-TT injected (FIG. 2). Black bars inside of nonimmunized control (0) bars represent organ weights of castrated male rats of comparable age and body weight. Organ weights of all groups of immunized rats injected with 10, 50, 175 or 612 μg $LHRH_{10}$-TT are significantly lower than in nonimmunized controls and rats injected with 2.5 or 5 μg $LHRH_{10}$-TT ($P<0.0001$).

Figure 3A:
FIG. 3(A–D), discussed in Examples 6 and 9, depict pictures of cross sections of the testes of untreated control rat or rabbit (A, C) and rat immunized with $LHRH_{10}$-TT (B), or rabbit immunized with $LHRH_1$-TT (D).
Figure 3B:

Histological evaluations of cross-sections of the testes showed severe impairment of spermatogenesis in rats immunized with 10 μg $LHRH_{10}$-TT or more, as manifest by reduced diameters of seminiferous tubules (approximately one-fourth of those of nonimmunized controls) and atrophied Leydig and Sertoli cells. Doses of 2.5 and 5 μg/rat of $LHRH_{10}$-TT had no effect on testicular functions. FIG. 3(A) shows a cross section of a rat testis from a nonimmunized control. FIG. 3(B) shows a cross section of a rat testis from a rat immunized with 10 μg/rat of $LHRH_{10}$-TT. Note the significantly reduced diameter of the seminiferous tubules and atrophied Leydig and Sertoli cells. Spermatogenesis did not progress beyond the spermatogonial stage in the immunized rat.

This Example shows that vaccination with $LHRH_{10}$-TT suppresses serum T levels in animals but not before 20 weeks of treatment.

EXAMPLE 7

Effects of increasing doses of $LHRH_1$-TT Vaccine

Three groups of rats (12/group) were immunized against LHRH using 50, 175, or 612 μg of $LHRH_1$-TT conjugate per rat. The adjuvant (MDP A-5), emulsifier (TP), immunization, and blood collection schedule were the same as in Example 6.

Figure 4:
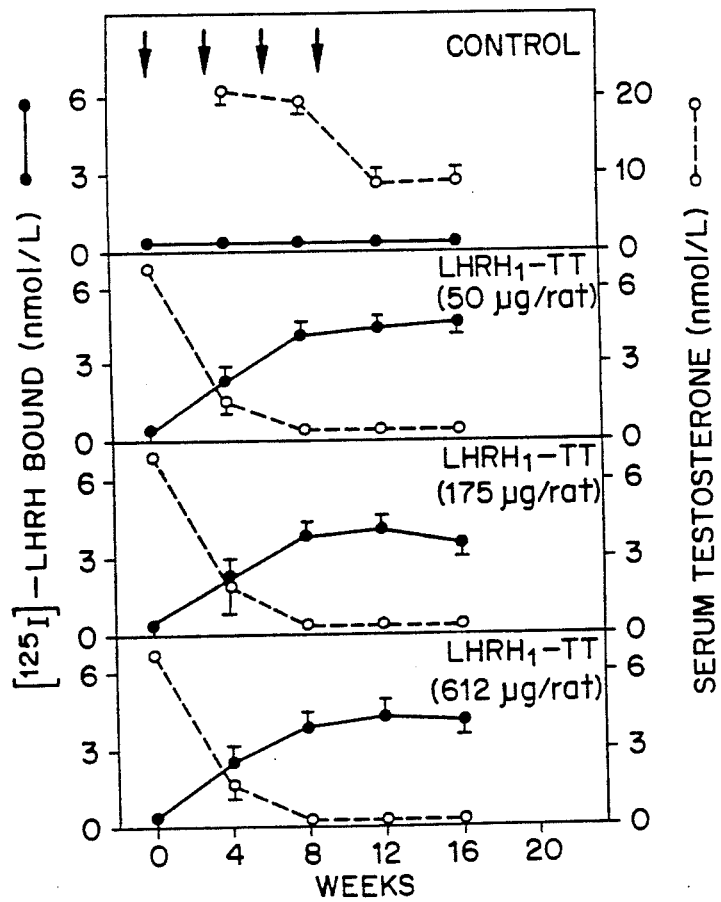
FIG. 4, discussed in Example 7, is a compilation of graphics comparing antibody titers and serum testosterone levels in rats immunized with increasing doses of $LHRH_1$-TT (ng/mL, mean±SE, n=11–12) from time zero to 16 weeks after immunization.

Animals immunized with $LHRH_1$-TT developed AT levels ranging from 2.0 to 2.4 nmol/L by week 4, and responded to the following booster injections by rapidly increasing AT. By week 8, unlike the animals in Example 6, AT levels exceeded 3.5 nmol/L (FIG. 4) in all three groups of immunized animals, regardless of the dose of $LHRH_1$-TT utilized in this experiment.

Figure 5:
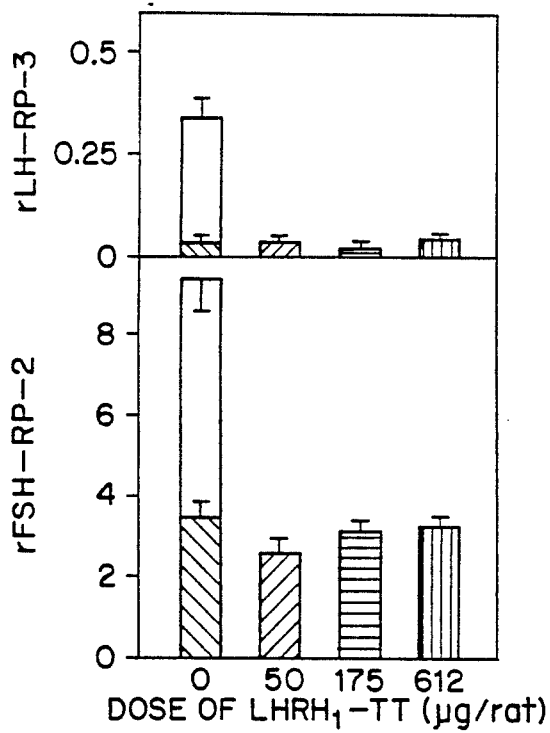
FIG. 5, discussed in Example 7, is a bar graph comparing serum LH and FSH levels in rats immunized with increasing doses of $LHRH_1$-TT (ng/mL, mean±SE, n=11–12) 8 weeks after immunization.

Biological effects of active immunization against three doses of $LHRH_1$-TT used in this experiment were expressed as a reduction of serum T levels (FIG. 4) due to significantly suppressed levels of serum gonadotropins (FIG. 5). In FIG. 5, the black bars inside of the nonimmunized control bars (0) represent serum LH and FSH levels in hypophysectomized rats. In this experiment serum T levels were suppressed below the limits of RIA sensitivity ($<0.03$ nmol/L) by week 8 after the primary immunization in all three groups of immunized animals. By week 8, testes were reduced to less than 30% of normal size, as estimated by palpation in all groups of immunized rats.

This Example shows that vaccination with $LHRH_1$-TT suppresses serum T levels to castration levels by 8 weeks of treatment. This is 12 weeks sooner than vaccination with $LHRH_{10}$-TT. (Example 6). $LHRH_1$-TT thus works quickly and efficiently to suppress serum T levels.

EXAMPLE 8

Effects of LHRH conjugation site in rats

Rats (12/group) were immunized using subcutaneous injections of either $LHRH_1$-TT or $LHRH_{10}$-TT (50 μg/rat) emulsified in TP; MDP A-5 (250 μg/rat) was used as an adjuvant. Nonimmunized (control) rats received injections of MDP A-5 in TP only. Booster injections were given 3, 6, and 9 weeks after the primary immunization. The experiment was terminated 14 weeks after the primary immunization.

Figure 6:
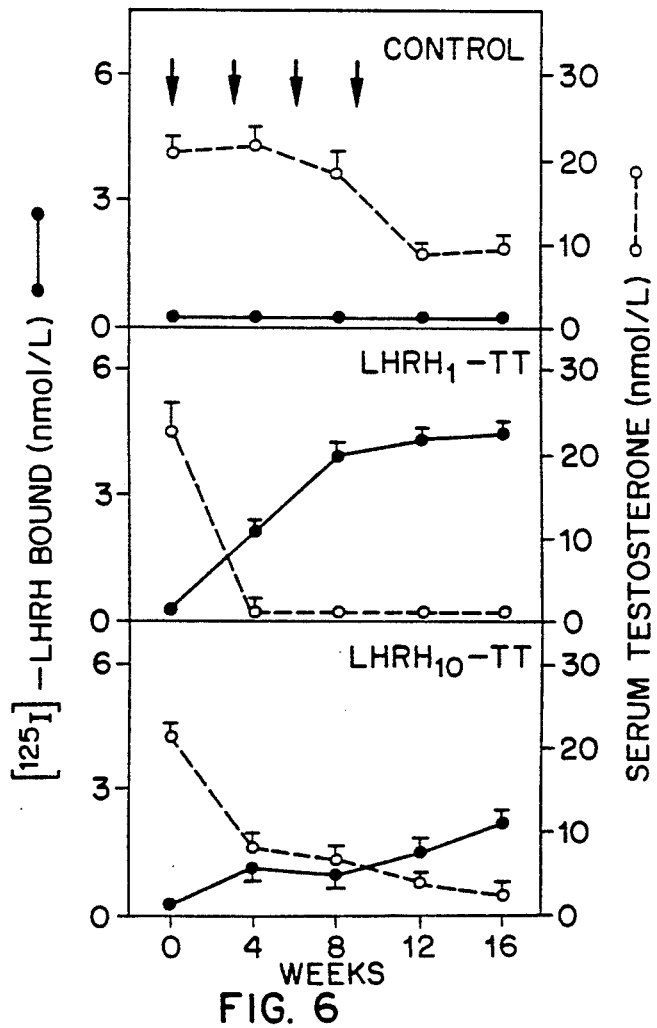
FIG. 6, discussed in Example 8, is a compilation of graphics comparing antibody titers and serum T levels in rats immunized with either $LHRH_1$-TT or $LHRH_{10}$-TT at a dosage of 50 μg/animal (mean±SE, n=10–12). Controls were injected with vehicle only. Arrows represent the time of injections of the selected conjugate.

Both immunological and biological effects were monitored. The results presented in FIG. 6 show that four weeks after primary immunization, rats immunized against $LHRH_1$-TT developed AT levels of $2.1 \pm 0.1$ nmol/L (mean±SE, n=12). By week 8, AT reached 4 nmol/L and remained above this level until the end of the experiment. Rats immunized against LHRH10-TT developed AT levels of approximately 2 nmol/L only by week 16, and the levels of AT in this group never exceeded 3 nmol/L.

The biological effects were evidenced in serum T levels and testes size reduction. Serum T levels in 11 of 12 rats immunized against $LHRH_1$-TT were suppressed to castration level by week 4. By week 8, all 12 rats in this group had nondetectable serum T levels and had testes reduced down to approximately 30 percent of normal size. Although serum T levels were significantly reduced (2.3±0.5 nmol/L) as compared with pre-immunization level (20.8±2.4 nmol/L) in the LHRH$_{10}$-TT-immunized group, none of the rats had levels below 0.03 nmol/L even sixteen weeks after the primary immunization. At this time, 5 of 12 rats had reduced testicular size, but not below 50% of normal and serum T levels ranging from 0.3 to 0.6 nmol/L.

This Example shows that LHRH$_1$-TT reduces serum T levels to castration levels in almost 100% of subjects by 4 weeks and 100% of animals by 8 weeks, whereas LHRH$_{10}$-TT does not reduce serum T levels to castration levels in the subjects even sixteen weeks after immunization. LHRH$_1$-TT is thus more effective and acts more rapidly than LHRH$_{10}$-TT indicating that LHRH$_1$-TT is more suited to treatment of patients requiring reduction of gonadotropic hormone levels.

EXAMPLE 9

Effects of the LHRH conjugation site in rabbits

Rabbits (6/group) were immunized by subcutaneous injection of 500 µg of conjugate (LHRH$_1$-TT, LHRH$_6$-TT, or LHRH$_{10}$-TT) emulsified in TP MDP A-5 was used as an adjuvant in a dose of 200 µg/rabbit. Nonimmunized controls were injected with MDP A-5 emulsified in TP only. Booster injections were given 3, 6, and 9 weeks after primary immunization at week 0. Blood was collected from the central ear artery every other week.

Figure 7:
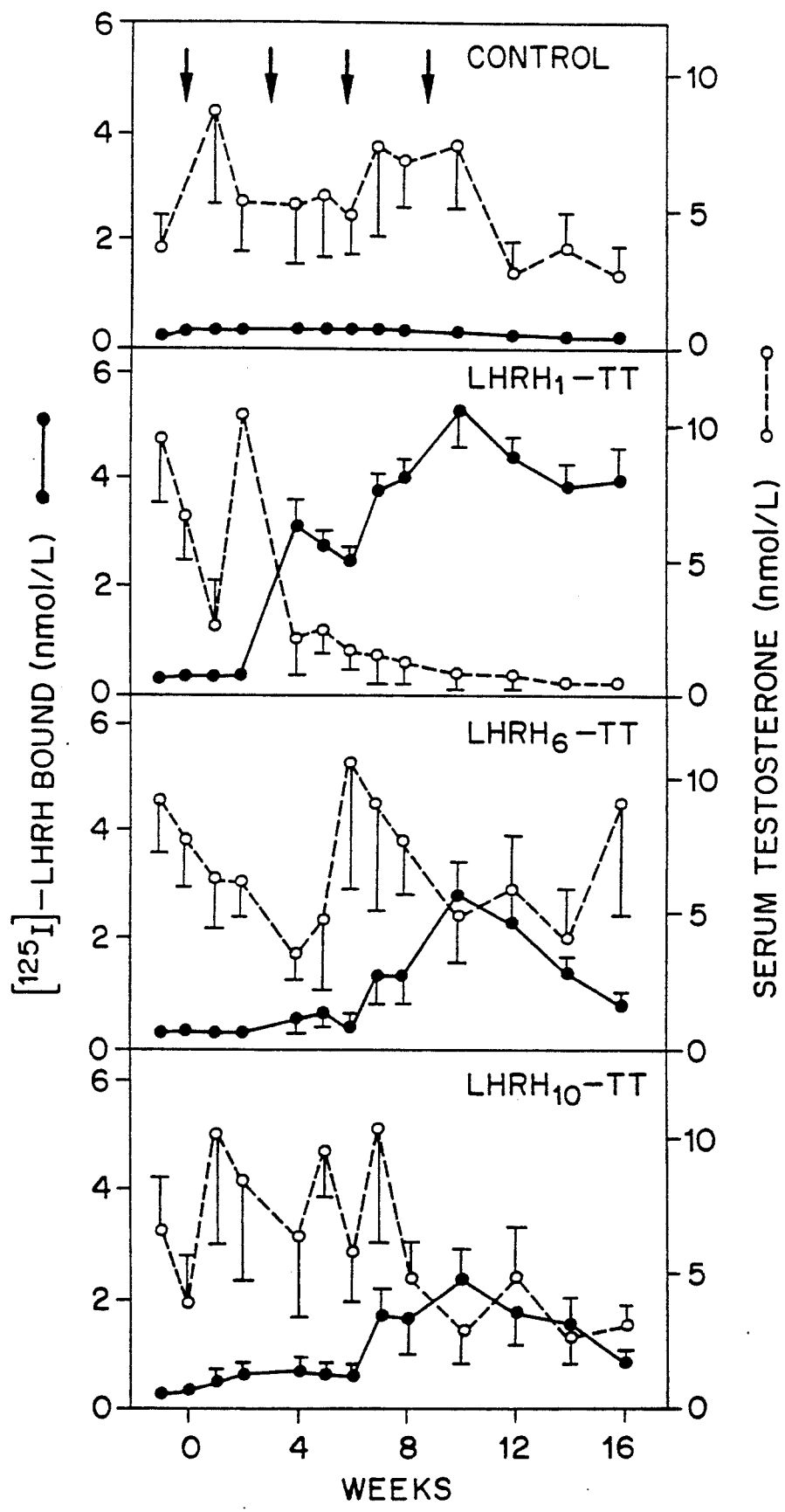
FIG. 7, discussed in Example 9, is a compilation of graphs comparing antibody titers and serum testosterone levels in rabbits immunized with various LHRH-conjugates (mean+SE, n=6).

Immune responses to active immunization against various LHRH conjugates in rabbits were similar to those in rats: rabbits immunized against LHRH$_1$-TT had AT levels of 3.1±0.5 nmol/L 4 weeks after the primary immunization and responded to the following booster injections. At week 9, AT was 5.3±0.7 nmol/L and remained close to 4 nmol/L until the end of the experiment (FIG. 7). Rabbits immunized against HRH$_6$-TT had their maximum antibody titers (2.8±0.6 nmol/L) at week 10, 1 week after the last booster injection, followed by a rapid decline in antibody titer. Similar results (maximum AT of 2.4±0.5 nmol/L at week 10) were obtained in LHRH$_{10}$-TT-immunized rabbits.

At the end of the experiment (16 weeks after the primary immunization) an LHRH-challenge test was performed in order to evaluate whether circulating LHRH antibodies are capable of inhibiting LHRH-induced LH and FSH release. Rabbits were injected subcutaneously with 30 µg of LHRH (LH-FSH-RH, chloride form, batch #2, National Hormone and Pituitary Program) dissolved in 1 mL 0.9% NaCl. Blood from the central ear artery was collected at 0, 30, 60 and 120 minutes after the injection of LHRH. Sera were separated and stored at −20° C. for further serum LH and FSH analysis.

Figure 8A:
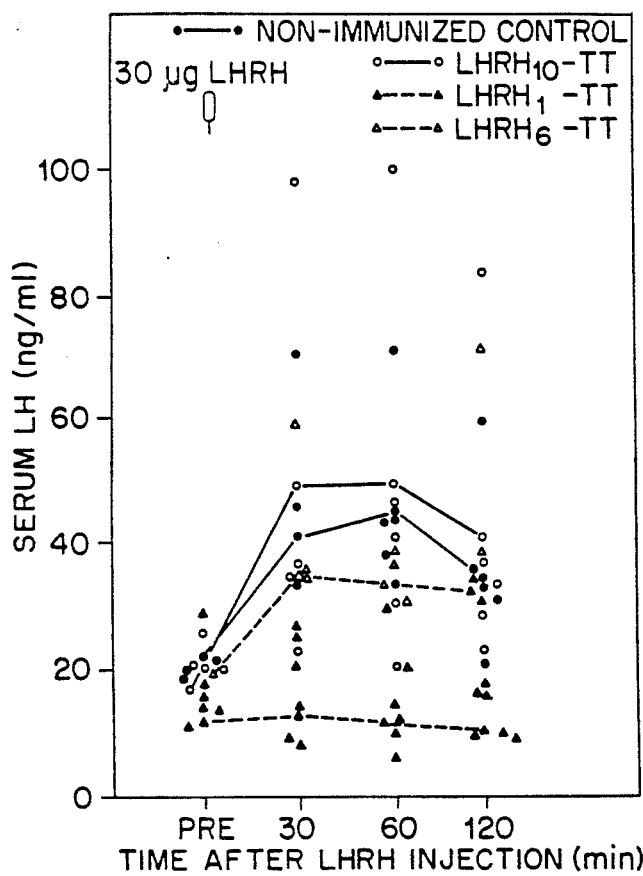
FIG. 8, discussed in Example 9, is two separate graphs FIGS. 8A and 8B depicting a response to LHRH-challenge test in rabbits immunized with various LHRH conjugates.
Figure 8B:
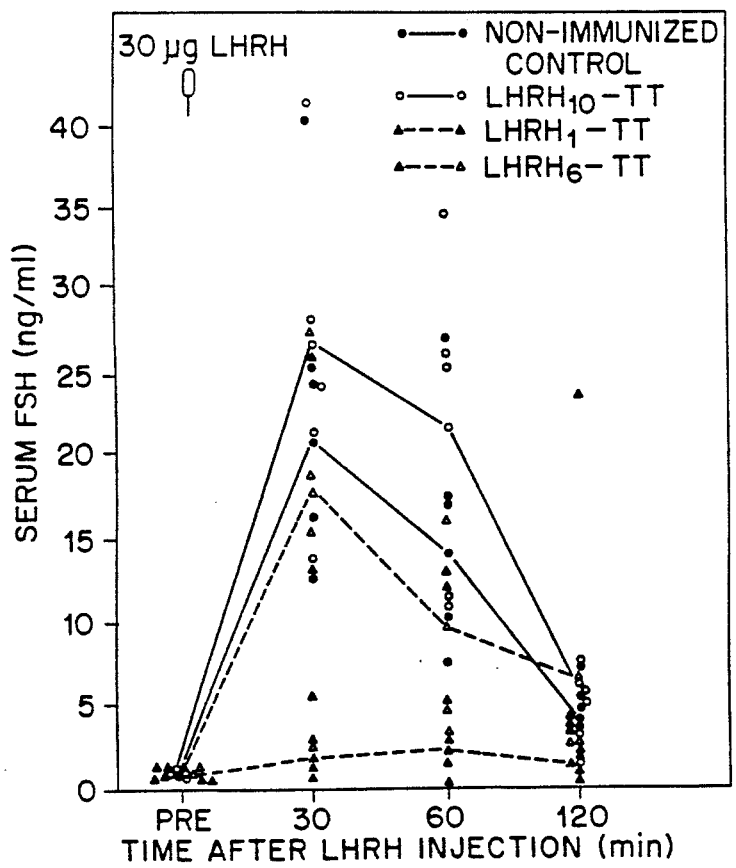

The LHRH-challenge test performed 16 weeks after the primary immunization revealed a lack of LH and FSH response to exogenous LHRH in LHRH$_1$-TT immunized rabbits (FIG. 8). In FIG. 8, lines represent mean values for each group of rabbits. Closed and open circles and triangles represent individual serum LH and FSH levels. In rabbits immunized with either LHRH$_6$-TT or LHRH$_{10}$-TT, changes in serum gonadotropins following the injection of LHRH were dependent on AT. Animals with AT levels above 1.0 nmol/L showed significantly suppressed pituitary LH and FSH response after injection of LHRH. However, only two rabbits immunized against LHRH$_{10}$-TT and two rabbits immunized against LHRH$_6$-TT had AT of ≧1 nmol/L; therefore, the mean increase of serum gonadotropins after the injection of LHRH in these two groups was not significantly different from controls.

Figure 3C:
Figure 3D:
Figure 9:
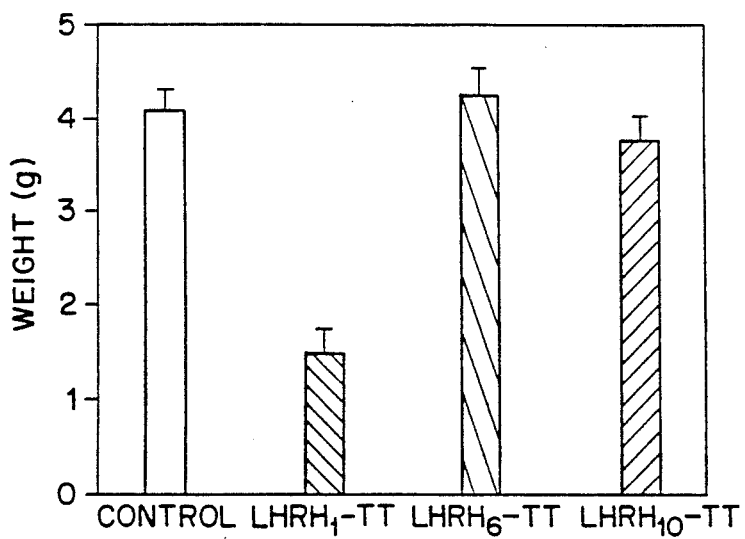
FIG. 9, discussed in Example 9, is a bar graph comparing testicular weights of rabbits immunized with various LHRH conjugates (mean±SE, n=6), the asterisk represents significantly (P<0.0001) reduced testicular weight over nonimmunized controls.
Figure 10:
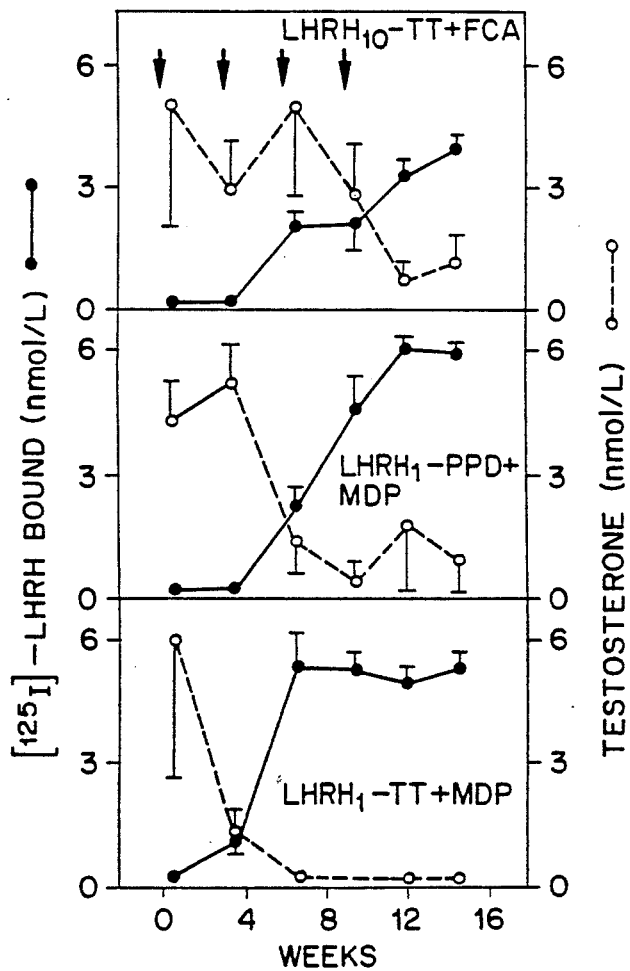
FIG. 10, discussed in Example 10, is a compilation of graphs comparing antibody titers and serum testosterone levels in rabbits immunized against LHRH conjugated at its N-terminus either to TT ($LHRH_1$-TT) or purified protein derivative ($LHRH_1$-PPD).

The biological effects of immunization using various LHRH conjugates are clearly demonstrated in the suppression of serum T levels While in the LHRH$_1$-TT-immunized group 5 of 6 rabbits had serum T at castration level at week 7, LHRH$_6$-TT- or LHRH$_{10}$-TT-immunized rabbits had serum T levels comparable with nonimmunized controls throughout the experiment (FIG. 7). Testicular weights in rabbits immunized against LHRH$_1$-TT were significantly reduced as compared with nonimmunized controls (FIG. 9). Histological evaluation of testicular cross-sections revealed arrest of spermatogenesis in this but not in two other groups of immunized rabbits (FIG. 3B). FIG. 3(C) shows a cross section of rabbit testis from a nonimmunized control rabbit. FIG. 3(D) shows a cross section of rabbit testis from a rabbit immunized with LHRH$_1$-TT. Note the significantly reduced diameter of the seminiferous tubules and the atrophied Leydig and Sertoli cells in the immunized rabbit. Spermatogenesis did not progress beyond the spermatogonial stage in the immunized rabbit.

The results of this experiment demonstrate that LHRH$_1$-TT acts more rapidly and efficiently than either LHRH$_6$-TT or LHRH$_{10}$-TT to reduce serum T levels to clinically significant levels.

EXAMPLE 10

Clinical Trials

Animal studies of the LHRH$_1$-TT vaccine have used 0.25 mg murabutide per injection in rats and rabbits. Human studies using murabutide in combination with tetanus vaccine gave best results using 0.05 mg/kg of approximately 3.1 mg per dose. The dose of 1.0 mg is selected for the first clinical study of the LHRH$_1$-TT vaccine.

The following are the drug substances used in manufacturing of the vaccine for human use and their release specifications:

(i)[Gln$^1$]-LHRH is obtained from the Clayton Foundation Laboratories for Peptide Biology, the Salk Institute, through the Contraceptive Development Branch of the National Institute for Child Health and Human Development. It is identified by high performance liquid chromatography with Bio-Sil T5K-250 column with 50 mM sodium sulfate in 20 mM phosphate buffer at pH 6.8 as the mobile phase. The compound should be a single peak by HPLC analysis with no more than 5% contamination of native LHRH. Tetanus toxoid is obtained from Wyeth Laboratories, Radnor, Pennsylvania. 1-Ethyl-3 (3-dimethylaminopropyl) carbodiimide hydrochloride is purchased from Sigma Chemical Company, St. Louis, Missouri. NaCl is provided by Mallinkrodt. Sodium phosphate monobasic is provided by Mallinkrodt. TWEEN 80 is purchased from Sigma Chemical Company, St. Louis, MI. PLURONIC L121 is purchased from BASF Wyandotte Corporation, Wyandotte, Michigan. Thimerasol is purchased from Roger Chemical Co., New Jersey.

The drug product is dispensed in two vials. One vial contains the [Gln$^1$]-LHRH-TT conjugate and the other vial contains a lyophilized powder of the adjuvant murabutide. A single dose of vaccine consists of 0.5 mL vaccine solution plus 1 mg murabutide.

The contents of the vaccine vial per 0.5 mL solution are as follows:

| (i) | [Gln¹]-LHRH-TT | 0.5 mg |
|---|---|---|
| (ii) | Sodium chloride | 4.4 mg |
| (iii) | Sodium phosphate, monobasic | 0.7 mg |
| (iv) | TWEEN 80 | 1.0 mg |
| (v) | PLURONIC L121 | 12.5 mg |
| (vi) | Thimerosal | 0.05 mg |

Each vaccine vial contains 0.7 mL, of which 0.5 mL are used per injection. The above list of contents is that contained in 0.5 mL.

The content of the murabutide vial is as follows:

| (i) Murabutide lyophilized powder | 5 mg |
|---|---|

Prior to administration, 0.25 mL of vaccine solution is removed aseptically from the vaccine vial with a 1 mL tuberculine syringe and added to the vial containing 5 mg murabutide powder. The murabutide vial is then gently agitated to dissolve the powder, creating a solution containing 1 mg murabutide per 0.05 mL. Then 0.05 mL of this solution is transferred from the murabutide vial into the 1 mL syringe. 0.45 mL of vaccine solution from the vaccine vial is added to the syringe. The total contents of the syringe, consisting of 0.5 mL vaccine solution and 1 mg murabutide, is administered intramuscularly by injection to each patient.

Preparation of [Gln¹]-LHRH-TT conjugate is as follows. A solution consisting of 150 mg [Gln¹]-LHRH, 150 mg TT and 750 mg 1-ethyl-3-(3-dimethylaminopropyl) carbodiimide hydrochloride in 60 mL of water is reacted at room temperature for 24 hours. The reaction mixture is dialyzed against 5 mM phosphate buffer at pH 7.4 for two days. The conjugate is filtered through a sterile filter unit (Falcon filter unit, 0.22 micron). The amount of [Gln¹]-LHRH-TT conjugate in the solution is determined by Lowry protein assay. The amount of LHRH in the conjugate is determined by radioimmunoassay.

Lowry protein assay:
(i) Reagents:
Reagent A: 2% $Na_2CO_3$ in 0.1 N NaOH
Reagent B1: 2% NaK tartrate
Reagent B2: 1% $CuSO_4 \cdot 5H_2O$
Reagent C: Mixture of Reagents A:B1:B2 (100:1:1)
Reagent E: 1 N phenol reagent (Fisher Scientific)
(ii) Procedure:
The protein standard is prepared from 1 mg/mL bovine serum albumin (BSA) stock solution to give concentrations of 25, 50, 75 and 100 µg/500 µL. Water is used as the blank tube. To each 500 µL sample tube, add 2.5 mL reagent C, vortex, and let stand for 10 minutes. Add 0.25 mL Reagent E, vortex and let stand for 30 minutes. Determine absorbancy at 540 nm. A standard curve is plotted using µg BSA concentration vs. 540 nm absorbance.
(iii) Concentration of [Gln¹]-LHRH-TT in the solution is determined based on the standard curve of BSA. Radioimmunoassay:
(i) Reagents:
[$^{125}$I]-LHRH: purchased from New England Nuclear, Boston, MA.
Antiserum: prepared by immunization of rabbits against [Gln¹]-LHRH-TT.
[Gln¹]-LHRH: supplied by Salk Institute.

Phosphate buffer - saline (PBS): 0.15 M NaCl, 0.01 M phosphate buffer at pH 7.5.
Bovine γ-globulin: 5 mg/mL.
Polyethyleneglycol: 25% solution.
(ii) Procedure:
Samples for standard curve are prepared by diluting [Gln¹]-LHRH to concentrations of 0.05, 0.1, 0.2, 0.4, 0.6, 1.0, and 2.5 ng/mL. The [Gln¹]-LHRH-TT conjugate is similarly diluted to 2, 5, 10, 30, 100 and 500 ng/mL. All samples are prepared in duplicate. 0.5 mL aliquots of the diluted standard, blank, and test samples are distributed to test tubes and 0 1 mL of a solution of [$^{125}$I]-LHRH containing about 50,000 cpm is added to each. 0.2 mL of the diluted antiserum is added to each except for one pair of blank tubes. 0.2 mL of 0.1 M EDTA in PBS is added to the blank pair.

The solutions are mixed thoroughly with a vortex mixer and incubated in a water bath at 37° C. for two hours and then overnight at 4° C. At the end of the incubation period, 0.2 mL of a solution containing 5 mg of bovine γ-globulin per mL and one mL of 25% polyethylene glycol in PBS are added and the solution thoroughly mixed with a vortex mixer. The mixture is then centrifuged at 2000×g for 40 min. The supernatant is decanted and precipitate counted in a gamma counter.

Counts are corrected by subtracting the counts found in the blank samples. The ratio of counts of test samples over counts without test sample ($B/B_o$) is plotted against a logarithmic scale of concentration of test samples. A regression line is drawn.

(iii.) Calculation of the amount of [Gln¹]-LHRH present in the [Gln¹]-LHRH-TT conjugate:

The aim of the assay is to determine the amount of [Gln¹]-LHRH-TT conjugate which is assayable by radioimmunoassay (RIA). [Gln]-LHRH is used as standard in the assay system. The corresponding molar amount of assayable [Gln¹]-LHRH on [Gln¹]-LHRH-TT is measured and expressed as the molar ratio of [Gln¹]-LHRH to [Gln¹]-LHRH-TT. The amount of [Gln¹]-LHRH is an underestimate of its actual amount in [Gln¹]-LHRH-TT because the conjugated [Gln¹]-LHRH (MW 1.2kD) in the interior part of the tetanus toxoid (MW 150kD) is not accessible to the antibody in this RIA system.

The concentration of [Gln¹]-LHRH and [Gln¹-LHRH-TT corresponding to 50% inhibition of binding of [$^{125}$I]-LHRH is determined from the $B/B_o$ vs logarithm of concentration curve. The molecular weight of [Gln¹]-LHRH and [Gln¹]-LHRH-TT are $1.2 \times 10$ and $1.5 \times 10$ Daltons respectively. The molar ratio of [Gln¹]-LHRH/ [Gln¹]-LHRH-TT is obtained by:

$$\frac{\text{moles [Gln}^1] - LHRH}{\text{moles [Gln}^1] - LHRH - TT} = $$

$$\frac{\frac{ng\ [Gln^1] - LHRH\ \text{of 50\% binding inhibition}}{1.2 \times 10^3}}{\frac{ng\ [Gln^1] - LHRH - TT\ \text{of 50\% binding inhibition}}{1.5 \times 10^5}}$$

(iv.) Control specification of [Gln¹]-LHRH-TT:
The molar ratio of [Gln¹]-LHRH: [Gln¹]-LHRH-TT should be more than 1.
High performance liquid chromatography (HPLC):
(i.) Column reagents and procedures:
column: Bio-Sil TSK-250 (300×7.5 mm), purchased from Bio Rad Mobil phase: 50 mM sodium sulfate, 20 mM phosphate buffer (pH 6.8)
Flow rate: 1.0 mL per minute
Chart speed: 5 min/cm
Detector: 254 nm
Loop size: 20 μL.
(ii.) Control specification of [Gln$^1$]-LHRH-TT:
No unreacted [Gln$^1$]-LHRH is present in the product
One major broad peak with shoulder.

Subjects are men with metastatic prostate cancer (Stage D2) who have undergone orchiectomy. History, physical exam including vital signs and performance status and laboratory tests of hematology, chemistry, and endocrine function are performed prior to immunization. They are repeated on the day of each of the three immunizations, every four weeks thereafter for the first six months of the study, and then every three months for up to two years. In subjects with measurable disease, X-rays or scans are done prior to immunization, on the day of the third immunization, and every four weeks thereafter. Pathology reports are reviewed on all subjects. Subjects requiring radiation or chemotherapy in the first eight weeks of the study, and those developing signs of immediate hypersensitivity or signs of systemic, renal, hematologic, endocrinologic, or neurologic adverse effects receive no further immunizations, but are followed for 6 months. Subjects with a history of autoimmune disease or hypersensitivity to tetanus toxoid, with brain metastases documented within 6 months prior to enrollment, or who are undergoing radiation or chemotherapy are not enrolled in the study.

Blood samples are drawn on the day of the initial immunization and at 2, 4, 8, 12, 16, 20 and 24 weeks, and every 3 months thereafter (for up to 2 years) for use in assays to detect antibody titers to LHRH. Each sample for this is 10 mL of blood collected in an non-anticoagulant treated tube. This sample is allowed to clot over approximately one hour at room temperature and the serum collected after centrifugation. This sample is frozen at −20° C.

Blood samples are drawn on the day of the initial immunization and at 2, 4, 8, 12, 16, 20 and 24 weeks and every 3 months thereafter (for up to two years) for use in radioimmunoassays to detect serum LH, FSH, growth hormone, prolactin, and testosterone levels. Each sample is 10 mL of blood collected in an non-anticoagulant treated tube. This sample is allowed to clot over approximately one hour at room temperature and the serum collected after centrifugation. This sample is either immediately assayed as described in Example 3 or frozen at −20° C. and subsequently assayed.

If the tumor is measurable then evaluation is done at 4 week intervals. These examinations allow a quantitative assessment of the disease extent. Criteria for response are the standard SWOG criteria.

EXAMPLE 11

Comparison of Adjuvant-Effects of Murabutide, MDP A-5 and a Mixture of Tween 80 and Pluronic (TP)

In order to determine whether MDP A-5 or Murabatide were more effective at inducing antigenicity, rats were injected with MDP A-5 in TP (250 μg/rat) or Murabutide in TP (250 μg/rat) as described in Example 6. The results obtained are shown in Table 1. Antibody titers were determined as described in Example 3.

TABLE 1

| Group No. | Batch of LHRH$_1$-TT Conjugate | Conjugate (dose) | Adjuvant (dose) |
|---|---|---|---|
| 1 | x-19 | 50 μg/rat | MDP in TP (250 μg/rat) |
| 2 | x-19 | 50 μg/rat | Murabutide in TP (250 μg/rat) |

| | Antibody Titers (nmol/L, mean ± SE, N = 6 to 7) at week: | | |
|---|---|---|---|
| | 3 | 5 | 7 |
| Group 1 | 2.0 ± 0.3 | 3.7 ± 0.5 | 3.4 ± 0.5 |
| Group 2 | 1.5 ± 0.3 | 3.2 ± 0.4 | 3.3 ± 0.2 |
| | Serum testosterone (nmol/L, mean ± SE, N = 6 to 7) | | |
| Group 1 | 1.7 ± 0.6 | 0.03 ± 0 | 0.03 ± 0 |
| Group 2 | 4.4 ± 1.5 | 0.03 ± 0 | 0.03 ± 0 |

Testes Weights (g) (Mean ± SE, N = 6)
Group 1: 0.74 ± 0.12
Group 2: 0.50 ± 0.04
(Control: 1.7 ± 0.03)

No significant differences were observed in antibody titers, serum testosterone levels or sex organ weights (at week 7) between MDP A-5 and Murabutide.

In order to determine whether MDP A-5 or TP were contributing to antigenicity, rats were injected as above with one of the following: TP (no adjuvant); MDP A-5 (250 μg/rat) in TP; and MDP A-5 in SPAN 80 (Sorbitan monoleate, (Ruger Chemical Co., Irvington NJ) and TWEEN 80. The TP and MDP/A-5 injections were prepared as described in Example 6; MDP A-5 in SPAN 80 and TWEEN 80 were prepared by mixing all the components in an electric blender until an emulsion was achieved. The final injections contained 12 mg TWEEN 80, 48 mg SPAN 80, 0.34 ml H$_2$O, 0.66 ml peanut oil and 175 μg LHRH$_1$-TT. Antibody titers were determined as described in Example 3. The results obtained are shown in Table 2.

TABLE 2

| Group No. | Batch of LHRH$_1$-TT Conjugate | Conjugate (dose) | Adjuvant (dose) |
|---|---|---|---|
| 1 | YT-1X-140 | 175 μg/rat | TP (no adjuvant) |
| 2 | YT-1X-140 | 175 μg/rat | MDP A-5 (250 μg/rat) in TP |
| 3 | YT-1X-140 | 175 μg/rat | MDP A-5 (250 μg/rat) SPAN 80 and TWEEN 80 |

| | Antibody Titers (nmol/L) (Mean ± SE, N = 10 to 12) at weeks: | | | |
|---|---|---|---|---|
| Group | 4 | 8 | 12 | 16 |
| 1 | 2.0 ± 0.1 | 3.8 ± 0.2 | 4.0 ± 0.3 | 3.0 ± 0.3 |
| 2 | 1.5 ± 0.1 | 4.5 ± 0.2 | 4.6 ± 0.2 | 4.2 ± 0.3 |
| 3 | 1.1 ± 0.1 | 2.7 ± 0.3 | 3.0 ± 0.3 | 2.0 ± 0.4 |

| | Serum Testosterone (nmol/L, Mean ± SE, N = 10 to 12) Week | | | |
|---|---|---|---|---|
| Group | 4 | 8 | 12 | 16 |
| 1 | 3.4 ± 1.5 | 0.03 ± 0 | 0.3 | 0.03 |
| 2 | 5.3 ± 1.6 | 0.1 ± 0.05 | 0.03 | 0.03 |
| 3 | 7.4 ± 1.7 | 4.0 ± 1.4 | 1.3 ± 0.6 | 7.0 ± 2.6 |

The results of this study demonstrate that, although animals in Group 2 (MDP A-5 used for all injections) have developed slightly higher antibody titers then those in Group 1 (LHRH$_1$-TT emulsified in TP without addition of adjuvant), serum testosterone levels were sufficiently suppressed in both groups by week 8. In contrast, animals in Group 3 (LHRH$_1$-TT emulsified in SPAN 80+TWEEN 80 with MDP A-5) developed significantly lower antibody titers and serum testosterone levels were not suppressed even by week 16.

This suggests that the presence of TP in immunogen is more important than the presence of MDP A-5.

In order to determine the importance of TP, rats were immunized with either MDP A-5 in TP or MDP A-5 in SPAN 80 plus alum. Antibody titers were obtained and the results were compared. The MDP A-5 TP injections were prepared as described above. The MDP A-5 alum injections were prepared as follows. The LHRH$_1$-TT was dissolved in phosphate buffered saline (PBS, 10 mM NaPO$_4$, 150 mM NaCl pH 7.2) to obtain a final concentration of 0.5 mg/ml. To the LHRH$_1$-TT/PBS solution was added 0.4 mL 10% AlK(SO$_4$)$_2 \times$10H$_2$O per mg of protein. A 7.5% NaHCO$_3$ solution was added to obtain maximum precipitation and the product was mixed well and centrifuged at 2,000 rpm for 10 minutes. After centrifugation the supernatant was discarded, the pellet was washed twice and resuspended in the vehicle to the desired concentration. Animals were injected and bled as described in Example 6 and antibody titers were determined as described in Example 3. The results obtained are shown in Table 3.

TABLE 3

| Group No. | Batch of LHRH$_{10}$-TT Conjugate | Conjugate (dose) | Adjuvant (dose) |
|---|---|---|---|
| 1 | YT-1X-122 | 175 µg/rat | MDP A-5 (250 µg) in TP |
| 2 | YT-1X-122 | 175 µg/rat | MDP A-5 (250 µg) in Span 80 + Alum |

| | Antibody Titers (nmol/L, mean ± SE, N = 11 to 12) at weeks: | | | |
|---|---|---|---|---|
| Group | 4 | 8 | 12 | 20 |
| 1 | 1.1 ± 0.3 | 1.0 ± 0.1 | 1.6 ± 0.2 | 2.9 ± 0.2 |
| 2 | 1.6 ± 0.4 | 1.8 ± 0.2 | 1.7 ± 0.2 | 2.7 ± 0.2 |

| | Serum Testosterone (nmol/L, mean ± SE, N = 10 to 12) at week: | | | |
|---|---|---|---|---|
| Group | 4 | 8 | 12 | 20 |
| 1 | 7.3 ± 0.5 | 8.5 ± 1.4 | 3.4 ± 0.8 | 0.8 ± 0.3 |
| 2 | 8.1 ± 1.1 | 1.8 ± 0.5 | 3.3 ± 1.0 | 3.8 ± 1.0 |

Number of rats with serum testosterone levels below 0.03 nmol/L by week 20:
Group 1: 6 out of 12
Group 2: 1 out of 12

The results of this experiment, using LHRH$_{10}$-TT, clearly demonstrate the importance of TP in enhancing an immune response to LHRH.

EXAMPLE 12

Induction of Anti-LHRH Antibodies in Female Cats

Figure 11:
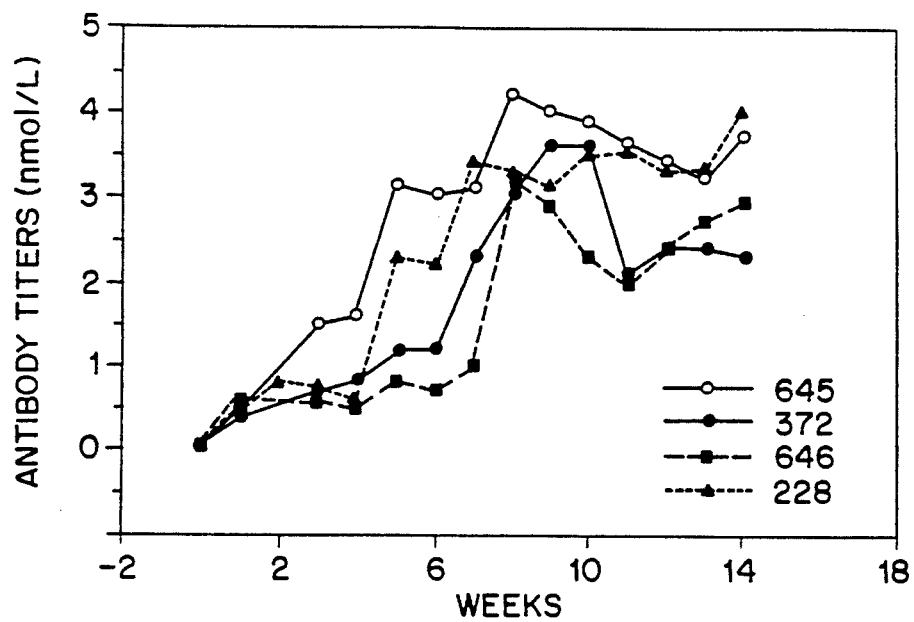
FIG. 11 is a graph depicting the LHRH antibody titers of female cats immunized with $LHRH_1$-TT as described in Example 12.
Figure 12A:
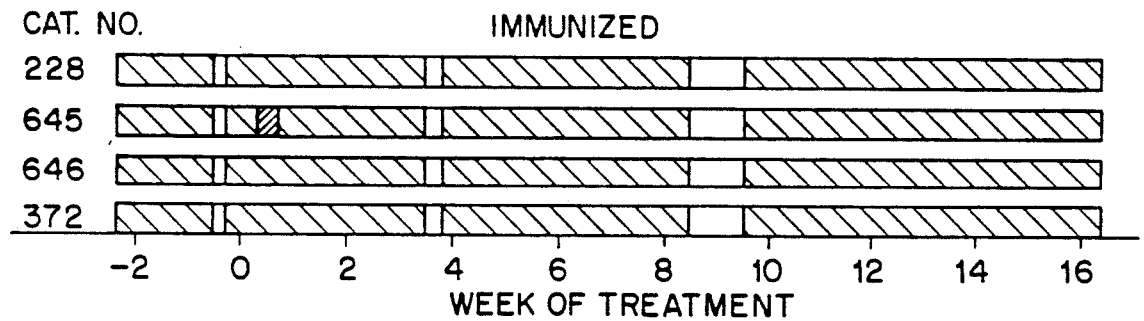
FIG. 12 (A and B), described in Example 12 are bar graphs depicting the estrous cycles of female cats immunized with $LHRH_1$-TT (A) or non-immunized animals (B).
Figure 12B:
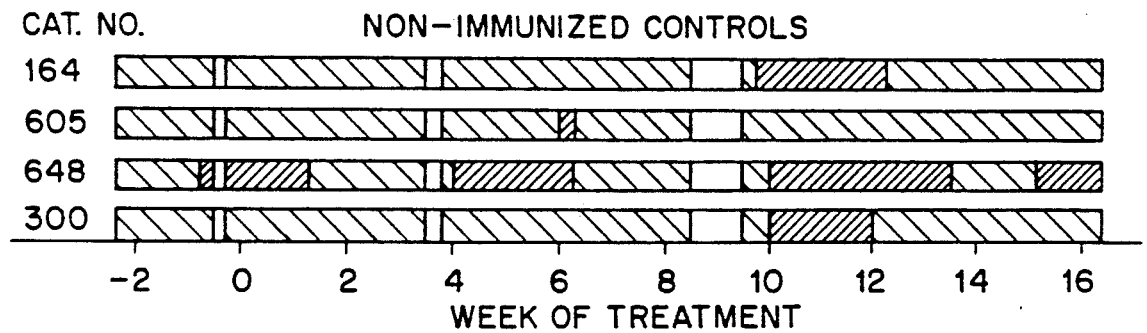

Four sexually mature female cats were immunized against LHRH$_1$-TT, using 500 µg/injection, as described in Example 6, and four cats were used as non-treated controls. The animals were checked daily for signs of estrus. Antibody titers were determined as described in Example 3. All immunized cats developed measurable antibody titers by week 4. By week 8, antibody titers exceeded 2 nmol/L (FIG. 11). None of the immunized cats displayed any signs of estrus during the 16 weeks of the experimental period. Non-immunized cats displayed signs of estrus from one to four times (FIG. 12). In FIG. 12 dotted bars indicate time cats were tested for signs of estrus and black bars indicate the times cats displayed signs of estrus. In FIGS. 11 and 12 the numbers 645, 372, 646 and 228 indicate cats immunized with LHRH$_1$-TT. In FIG. 12, the numbers 164, 605, 648 and 300 indicate non-immunized controls. The animals were killed sixteen weeks after the initial immunization. Ovaries in the immunized cats were approximately one-tenth the size of those in non-immunized controls.

EXAMPLE 13

Active Immunization Against LHRH Prevents the Growth of Androgen-Dependent Prostatic Carcinoma In order to determine whether active immunization against LHRH can be used as treatment for androgen-dependent prostatic carcinoma the following experiment was performed.

Fifty male rats of the Copenhagen Fisher F$_1$ strain were implanted subcutaneously with Dunning R-3327 prostate carcinoma. This carcinoma cell line was obtained from Dr. Karr at the University of Miami, School of Medicine. Rats were outfitted with self-piercing numbered ear-tags and randomly assigned to one of the following groups:

Group 1—non-immunized controls
Group 2—non-immunized, treated with LHRH-34 (250 µg/kg/day) for 120 days
Group 3—immunized against LHRH$_1$-TT
Group 4—immunized against LHRH$_1$-TT and treated with LHRH-34 (an LHRH antagonist: [Ac-D2Nal$^1$, 4ClDPhe$^2$, D3Pal$^3$, Arg$^5$, DGlu$^6$ (Anisole Adduct), DAla$^{10}$]-LHRH (obtained 6 from Dr. Sundaram) like Group 2 for the first 21 days.

Tumor sizes were measured weekly. Immunization and/or treatment with LHRH-34 was initiated when tumors were at least 3cm$^2$ in size (19 weeks after insertion of the tumor cells.) Each of the above listed group of animals consisted of 4 rats with tumors from 3 to 4 cm$^2$, 4 rats with tumors from 4 to 8 cm$^2$ and 4 to 5 rats with tumors larger than 8 cm$^2$]. The results obtained from rats immunized with LHRH$_1$-TT and treated with LHRH-34 are shown in closed triangles. Note that the antibody titers in nonimmunized rats are within the shaded area and were 0.4 nmol/L.

Animals in Group 1 (non-immunized controls) were injected daily with sterile saline. Rats in Group 2 were injected daily with LHRH-34 (250 µg/kg/day) dissolved in 5% mannitol in bacteriostatic water (0.5 ml/rat). Rats from Groups 3 and 4 were immunized against LHRH$_1$-TT (50 µg/rat/injection) emulsified in a mixture of Tween 80 and Pluronic in 0.9% NaCl as described in Example 12. Immunogen injections were given at weeks 19, 21 and 23 after the implantation of Dunning prostate cancer cells. Animals in Group 4 were immunized as in Group 3 and concomitantly treated with LHRH-34 as in Group 2 for the first 3 weeks after immunization.

Blood from the central caudal artery was collected approximately every 3 weeks from the beginning of LHRH immunization/treatment. The experiment was terminated approximately 4 months after initiation of the treatment. Testes, epididymides, prostates and seminal vesicles were dissected and weighed.

Figure 13:
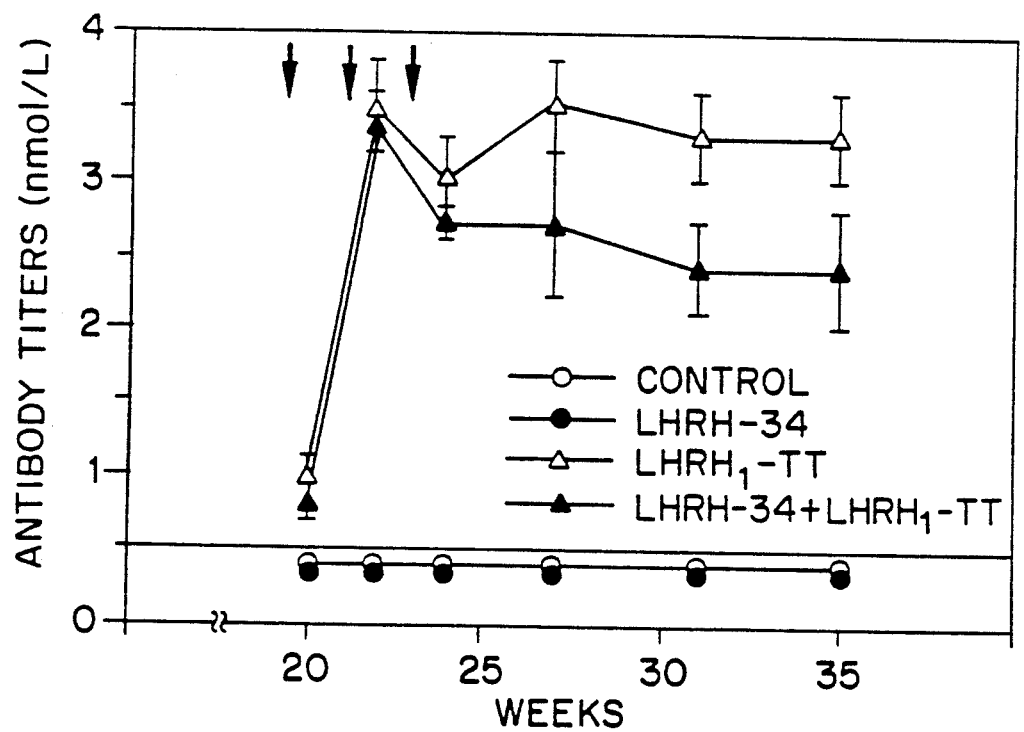
FIG. 13, described in Example 13, is a graph depicting Anti-LHRH antibody titers (mean±SE, N=11 to 12) in male rats bearing androgen-dependent, Dunnning R-3327 prostatic carcinoma. Arrows represent the time of immunization against LHRH. Antibody titers in non-immunized animals in the shaded area were 0.4 nmol/L.
Figure 14:
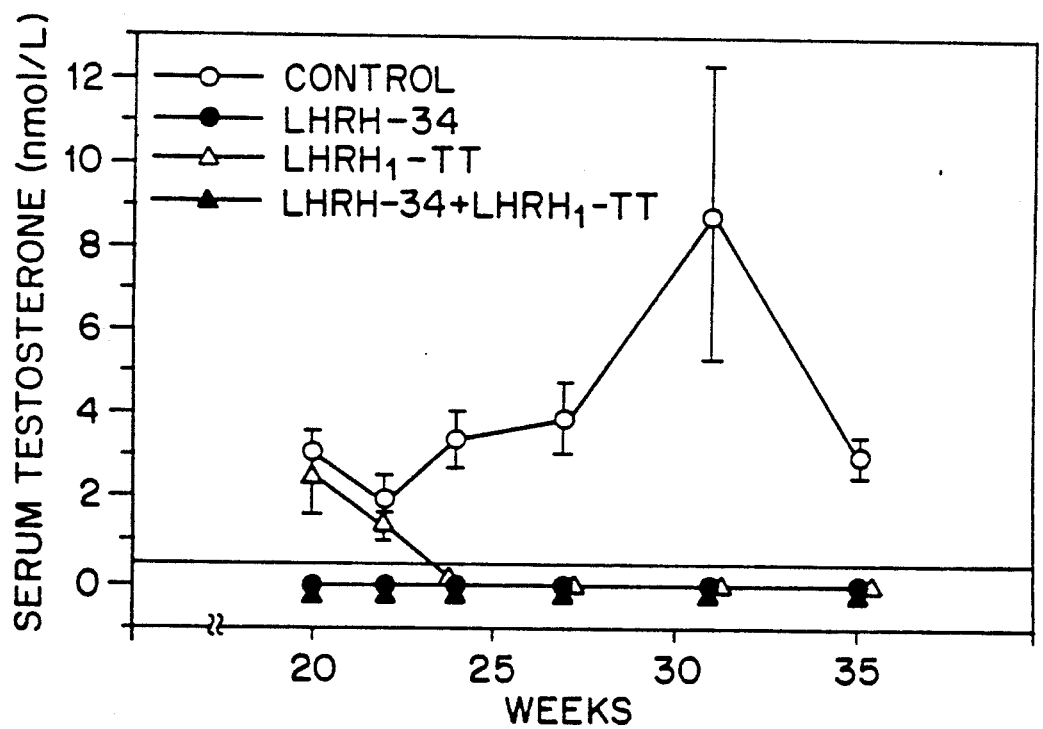
FIG. 14, described in Example 13, is a graph depicting serum testosterone (T) levels (mean±SE, N=11 to 12) in rats bearing androgen-dependent prostatic carcinoma. Treatment was initiated 19 weeks after insertion of cancer cells. Note immediate drop in serum T levels below 0.03 nmol/L in animals treated with LHRH-34 (closed circles and triangles in the shaded area). In animals immunized against $LHRH_1$-TT (open triangles) serum T levels dropped to castration level by week 24, five weeks after initial immunization.
Figure 15A:
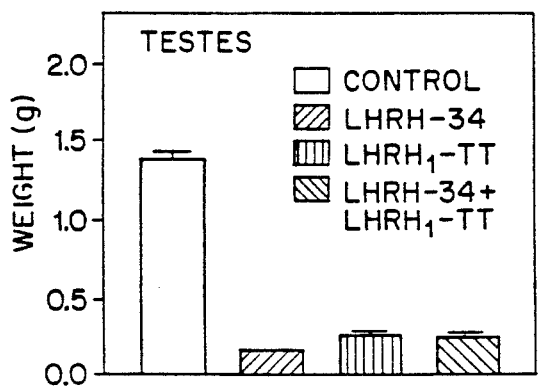
FIG. 15, described in Example 13, is a set of bar graphs FIGS. 15A, 15B, 15C and 15D depicting testes and accessory sex organ weights (mean ±SE, N=8 to 12) following 16 weeks of androgen suppression treatment.
Figure 15B:
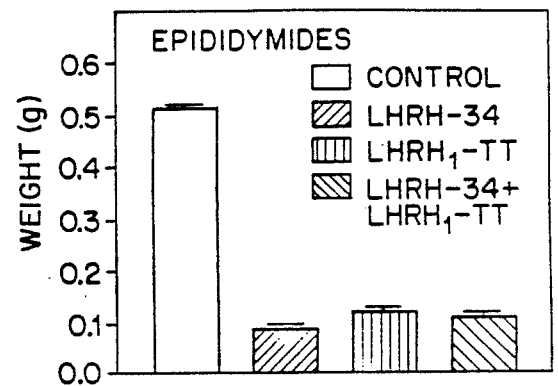
Figure 15C:
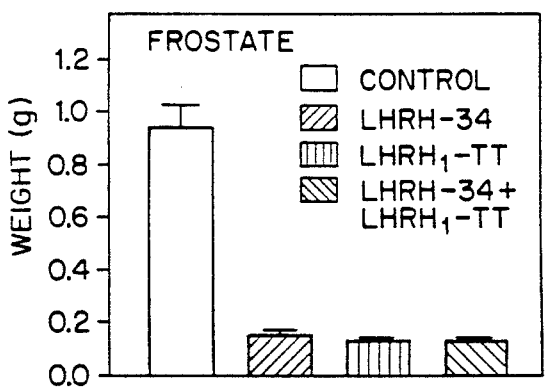
Figure 15D:
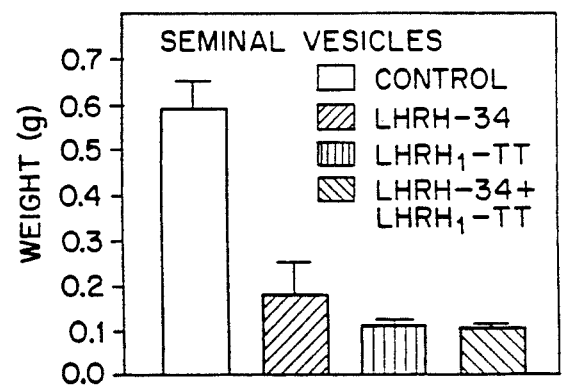

The results obtained showed that animals immunized against LHRH$_1$-TT (Groups 3 and 4) developed anti-LHRH anti-body titers above 3 nmol/L by week 22, only 3 weeks after the immunization (FIG. 13). FIG. 13 is a graph depicting the anti-LHRH antibody titers in the rats described above. Arrows represent the time of immunization against LHRH. The results obtained from the control rats are shown by the open circles. The results obtained from the rats treated with LHRH-34 are shown in closed circles. The results obtained from rats immunized with LHRH-TT are shown in open triangles. Animals from Group 4 (immunized against LHRH$_1$-T and concomitantly treated with LHRH-34) had anti-LHRH antibody titers lower than those without LHRH-34 treatment even after the LHRH-34 injections were discontinued. However, in both groups of immunized animals the amount of anti-LHRH antibodies was sufficient to suppress T to castration levels (below 0.03 nmol/L) by week 24. In animals treated with LHRH-34 alone serum T levels were suppressed by the time of the first blood collection at week 20 (FIG. 14). FIG. 14 is a graph depicting serum testosterone levels in the rats of the present example. The different groups are depicted as described above for FIG. 13. Note that immediately after treatment at nineteen weeks serum T levels dropped below 0.03 nmol/L in animals treated with LHRH-34 whereas in animals immunized with LHRH$_1$-TT serum T levels dropped to castration level by week 24, five weeks after initial immunization. All animals regardless of the treatment regimen, had serum T levels below 0.03 nmol/L through the end of the experiment at week 35. Testes and accessory sex organ weights in all groups of treated animals were significantly lower than those in non-immunized controls (FIG. 15). FIG. 15 is a series of bar graphs depicting organ weights of the various treatment groups following sixteen weeks of androgen suppression treatment. The control group is represented by the open bar, the LHRH treated group is represented by the slanted lines, the LHRH$_1$-TT immunized group is represented by the vertical lines and the LHRH-34 treated, LHRH$_1$-TT immunized group is represented by the cross-hatched bars. Note that the organ weights did not differ significantly between groups.

Figure 16:
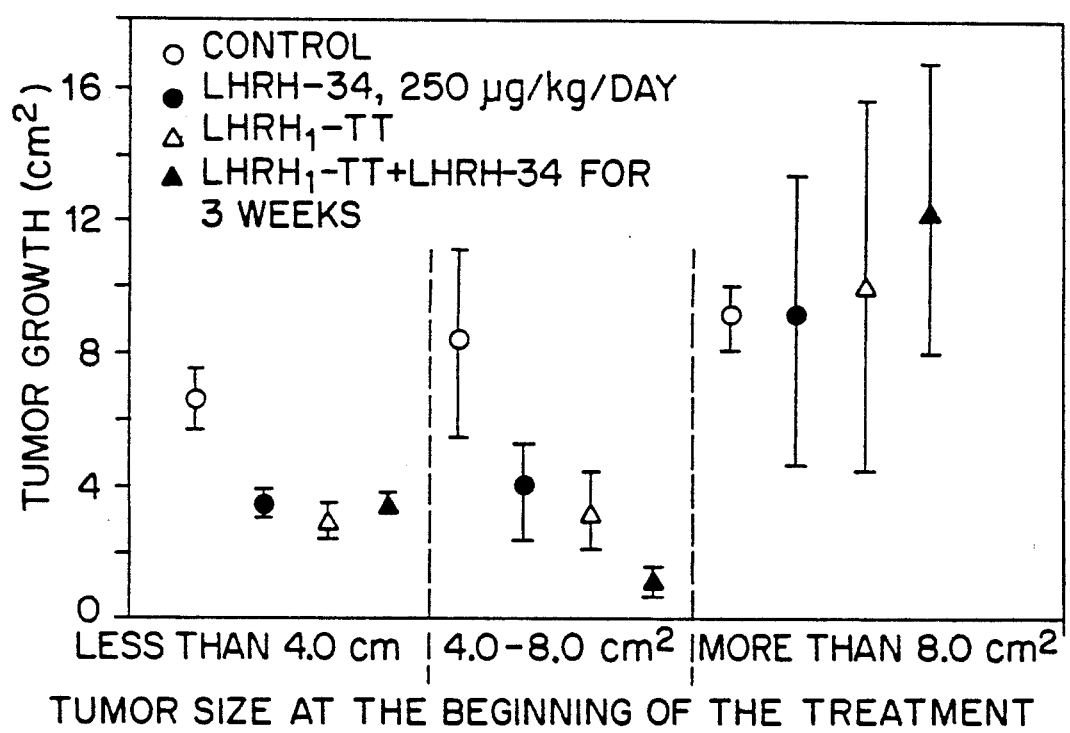
FIG. 16, described in Example 13, is a graph depicting suppression of growth of androgen-dependent prostatic carcinoma following 16 weeks of treatment expressed as the difference in tumor area (mean±SE, N=3 to 4) at beginning and end of treatment.

The effects of treatment with LHRH-34 and/or active immunization against LHRH on the growth of the tumors depended on tumor size. Androgen depletion through immunization against LHRH, daily injections with LHRH-34, or a combination of the two, resulted in significant suppression of tumor growth if treatment was initiated before tumors were larger than 8 cm$^2$. Once the tumors were larger than this size, however, neither immunization nor LHRH-34 treatment caused suppression of tumor growth (FIG. 16). FIG. 16 depicts the change in tumor size relative to initial tumor size for the various groups of rats. The difference is expressed as the difference in tumor area (mean+SE, N=3 to 4) at the beginning and end of treatment. The various groups are depicted as described above for FIG. 13.

The results presented above demonstrate that active immunization against LHRH can be successfully used as convenient and cost-effective treatment to suppress tumor growth in androgen-dependent prostatic carcinoma.

We claim:

1. A method for suppressing gonadotropic hormone release in a mammal comprising administering to the mammal [Gln$^1$]-luteinizing hormone releasing hormone conjugated to tetanus toxoid via the amino terminal glutamine in an amount effective to induce an immunogenic response to luteinizing hormone releasing hormone.

2. The method according to claim 1, wherein the mammal is a male and the suppression of gonadotropic hormone release in the mammal results in infertility.

3. The method according to claim 1, wherein the mammal is a male having androgen dependent carcinoma and the suppression of gonadotropic hormone release in the mammal is therapeutically effective in treating said carcinoma.

4. The method according to claim 3 wherein the mammal has a carcinoma selected from the group consisting of prostatic and testicular carcinomas.

5. The method according to claim 1, wherein the mammal is a male having prostatic hyperplasia and the suppression of gonadotropic hormone release in the mammal is therapeutically effective in treating said prostatic hyperplasia.

6. The method according to claim 1, wherein the mammal is a female having at least one of the indications selected from the group consisting of endometriosis, benign uterine tumors, recurrent functional ovarian cysts and severe premenstrual syndrome, and the suppression of gonadotropic hormone release in the mammal is therapeutically effective in treating said indication.

7. The method according to claim 1, wherein the therapeutic effect occurs within about 4 to about 8 weeks.

8. A vaccine composition comprising an immunologically effective amount of [Gln$^1$]-luteinizing hormone releasing hormone conjugated to tetanus toxoid via the amino terminal glutamine; Tween 80 (polyoxyetheylene (20) sorbitan monooleate); and Pluronic L121 (liquid block copolymer of propylene oxide and ethylene oxide, the liquid block copolymer having 15 weight percent ethylene oxide and a molecular weight of approximately $3.5 \times 10^3$).

9. The vaccine according to claim 8 wherein the Tween 80 and Pluronic L121 are present in a ratio of from 2:25 to 1:40.

10. A method for inducing infertility comprising administering to a mammal an immunologically effective amount of a vaccine comprising -luteinizing hormone releasing hormone conjugated to tetanus toxoid via the amino terminal glutamine.

11. A method according to claim 10, wherein the vaccine further comprises Tween 80 (polyoxyethylene (20) sorbitan monooleate) and Pluronic L121 (liquid block copolymer of propylene oxide and ethylene oxide, the liquid block copolymer having 15 weight percent ethylene oxide and a molecular weight of approximately $3.5 \times 10^3$).

12. A method for treating androgen dependent carcinoma in a mammal comprising administering to the mammal an immunologically effective amount of a vaccine comprising - luteinizing hormone releasing hormone conjugated to tetanus toxoid via the amino terminal glutamine.

13. A method according to claim 12, wherein the vaccine further comprising Tween 80 (polyoxyethylene (20) sorbitan monooleate) and Pluronic L121 (liquid block copolymer of propylene oxide and ethylene oxide, the liquid block copolymer having 15 weight percent ethylene oxide and a molecular weight of approximately $3.5 \times 10^3$).

14. A method for making an immunologically effective vaccine comprising mixing -luteinizing hormone releasing hormone conjugated to tetanus toxoid via the amino terminal glutamine with Tween 80 (polyoxyethylene (20) sorbitan monooleate) and Pluronic L121 (liquid block copolymer of propylene oxide and ethylene oxide, the liquid block copolymer having 15 weight percent ethylene oxide and a molecular weight of approximately $3.5 \times 10^3$).

15. The method according to claim 14, wherein the Tween 80 and Pluronic L121 are present at a ratio of from 2:25 to 1:40.

* * * * *

UNITED STATES PATENT AND TRADEMARK OFFICE
CERTIFICATE OF CORRECTION

PATENT NO. : 5,324,512

DATED : June 28, 1994

INVENTOR(S) : Ladd et al.

It is certified that error appears in the above-identified patent and that said Letters Patent is hereby corrected as shown below:

Title Page, Item 54, 3rd line, and Col. 1, 2nd line of title, "TETANUS" should read --TETANUS TOXOID--.

Title Page, Item 56, immediately after the heading "FOREIGN PATENT DOCUMENTS" insert:
--8606635    11/1986    World Int. Prop. O.
  2228262    8/1990     United Kingdom--

Title Page, 1st line of ABSTRACT, "prevention" should read --invention--.

Title Page, last line of ABSTRACT, "effect" should read --effective--.

Page 2 of the Title Page, column 2, 4th-from-bottom line, Immunication" should read --Immunization--.

Col. 1, line 7, insert the following information:
--This invention was made with the support of the United States Agency for International Development under Cooperative Agreement Number DPE-3050-A-00-8059-00 and from the National Institute of Child Health and Human Development Contract Number NO1-HD-3-3180 . The Government has certain rights in this invention--.

Col. 1, line 18, "Tests" should read --Testes--.

Col. 1, line 22, "Sandlet" should read --Sandler--.

Col. 2, line 5, "S18714" should read --S187- --.

Col. 2, line 15, "user" should read --use--.

UNITED STATES PATENT AND TRADEMARK OFFICE
CERTIFICATE OF CORRECTION

PATENT NO. : 5,324,512

DATED : June 28, 1994

INVENTOR(S) : Ladd et al.

It is certified that error appears in the above-identified patent and that said Letters Patent is hereby corrected as shown below:

Col. 2, line 65, "8-Subunit" should read --ß-Subunit--.

Col. 3, line 22, "Figure i(A)" should read --Figure 1(A)--.

Col. 3, line 49, "either" should read --either, or with--.

Col. 5, line 5, "thyroalobulin" should read --thyroglobulin--.

Col. 6, line 22, "CDS+" should read --CD8+--.

Col. 6, line 46, "monopoleate" should read --monooleate--.

Col. 6, line 53, "Tween 80 and Pluronic L121" should read --TWEEN 80 and PLURONIC L121--;

Col. 6, line 56, "Pluronics" should read --PLURONICS--.

Col. 6, line 59, "Anals" should read --Annals--.

Col. 8, line 54, "MO)." should read --MO.--]

Col. 10, line 60, "LHRH10-TT" should read --$LHRH_{10}$-TT--.

Col. 11, line 38, "$HRH_6$" should read --$LHRH_6$--.

Col. 12, line 60, "MI" should read --MO--.

Col. 13, line 9, "Thimerosal" should read --Thimerosol--.

Col. 13, line 48, "A:Bi:$B_2$" should read --A:$B_1$:$B_2$--.

UNITED STATES PATENT AND TRADEMARK OFFICE
CERTIFICATE OF CORRECTION

PATENT NO. : 5,324,512

DATED : June 28, 1994

INVENTOR(S) : Ladd et al.

It is certified that error appears in the above-identified patent and that said Letters Patent is hereby corrected as shown below:

Col. 14, bridging lines 49-50, "1.2 x 10 and 1.5 x 10" should read --1.2 x $10^3$ and 1.5 x $10^5$--.

Col. 15, bridging lines 63-64, "Murabatide" should read --Murabutide--.

Col. 16, line 66, "then" should read --than--.

Col. 18, line 41, "$cm^2$]." should read --$cm^2$.--]

Col. 19, line 9, "$LHRH_1$-T" should read --$LHRH_1$--TT--.

Col. 20, line 31, "Tween 80" should read --TWEEN 80--.

Col. 20, line 32, "Pluronic L121" should read --PLURONIC L121--.

Col. 20, line 42, "-luteinizing" should read --[$Gln^1$]-luteinizing--.

Col. 20, line 46, "Tween 80" should read --TWEEN 80--.

Col 20, line 47, "Pluronic L121" should read --PLURONIC L121--.

Col. 20, line 55, "-luteinizing" should read --[$Gln^1$]-luteinizing--.

Col. 20, line 59, "comprising Tween 80" should read --comprises TWEEN 80--.

UNITED STATES PATENT AND TRADEMARK OFFICE
CERTIFICATE OF CORRECTION

PATENT NO. : 5,324,512

DATED : June 28, 1994

INVENTOR(S) : Ladd et al.

It is certified that error appears in the above-identified patent and that said Letters Patent is hereby corrected as shown below:

<u>Col. 20, line 60</u>, "Pluronic L121" should read --PLURONIC L121--.

<u>Col. 20, line 66</u>, "-luteinizing" should read --[GLN$^1$]-luteinizing--.

<u>Col. 22, line 4</u>, "Tween 80 and Pluronic L121" should read --TWEEN 80 and PLURONIC L121--.

Signed and Sealed this

Twenty-eight Day of February, 1995

Attest:

BRUCE LEHMAN

Attesting Officer

Commissioner of Patents and Trademarks